(12) United States Patent
Hölzl et al.

(10) Patent No.: US 7,105,577 B2
(45) Date of Patent: Sep. 12, 2006

(54) ANTIMICROBIAL METHOD USING A HYDROXYDIPHENYL ETHER COMPOUND

(75) Inventors: Werner Hölzl, Eschentzwiller (FR); Wolfgang Haap, Grenzach-Wyhlen (DE); Dietmar Ochs, Schopfheim (DE); Karin Puchtler, Fischingen (DE); Marcel Schnyder, Birsfelden (CH); Surendra Umesh Kulkarni, Mumbai (IN); Arakali Srinivasarao Radhakrishna, Bangalore (IN); Mangesh Shivram Sawant, Mumbai (IN); Asawari Bhikaji Mahtre, Mumbai (IN)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/816,967

(22) Filed: Apr. 2, 2004

(65) Prior Publication Data

US 2004/0186174 A1 Sep. 23, 2004

Related U.S. Application Data

(63) Continuation of application No. 10/281,011, filed on Oct. 25, 2002, now abandoned, which is a continuation of application No. 09/573,403, filed on May 18, 2000, now abandoned.

(30) Foreign Application Priority Data

May 20, 1999 (EP) .................................. 99810442

(51) Int. Cl.
*A61K 31/075* (2006.01)
*A61K 31/12* (2006.01)

(52) U.S. Cl. ...................... 514/721; 514/679; 514/880; 514/881; 514/901; 424/49; 424/76.8

(58) Field of Classification Search ................ 514/679, 514/721, 880, 881, 901; 424/49, 76.8
See application file for complete search history.

(56) References Cited

U.S. PATENT DOCUMENTS 3,753,914 A 8/1973 Berth et al. ................... 252/95
4,238,626 A 12/1980 Nahm et al. ................. 562/472
4,268,693 A 5/1981 Muntwyler et al. ......... 568/637
4,980,153 A 12/1990 Jackson et al. ............... 424/52

FOREIGN PATENT DOCUMENTS

| CH | 148291 | 10/1931 |
| DE | 1288747 | 2/1969 |
| DE | 2538016 | 3/1977 |
| JP | 09135893 | 5/1997 |

OTHER PUBLICATIONS

Silverman, The Organic Chemistry of Drug Design and Drug Action, 1992, pp. 15-19.*
Chem. Abstr. vol. 76, No. 1, (1972) 2525t.
Hayashi et al., Development . . . their activity, J. Agric. Food Chem., vol. 38(10), pp. 1965-1971.
Venkatasubbaiah et al., Phytotoxic metabolites of . . . pokeweed, Mycologia, vol. 84(5), abstract.
Iossifova et al., Antimicrobial effects . . . Fraxinus ornus bark, Pharmazie, vol. 49(4), abstract.
Heath et al., Broad Spectrum . . . acid synthesis, J. Biol. Chem., vol. 273(46), pp. 30316-30320.
Silverman, The Organic Chemistry of Drug Design and Drug Action, pp. 15-22.
S. Shapiro et al., Quantitative Structure-Activity Relationships, vol. 17, No. 4, (1998), pp. 327-337.
Chem. Abstr. of vol. 47, No. 4, 1644g for J. Pharm. Soc. Japan, vol. 72, (1952), pp. 300-303.
Fujikawa et al., Antiseptics for foods diphenyl ether derivatives . . . as a preservative for sake, Yakugaku Zasshi, 1971, vol. 91, (9), pp. 930-933, abstract.

* cited by examiner

*Primary Examiner*—Rosalynd Keys
(74) *Attorney, Agent, or Firm*—Joseph C. Suhadolnik

(57) ABSTRACT

The present invention relates to the use of hydroxydiphenyl ether compounds as antimicrobially active substances, to certain new compounds of this type and to processes for the preparation of these compounds.

11 Claims, No Drawings

ANTIMICROBIAL METHOD USING A HYDROXYDIPHENYL ETHER COMPOUND

This application is a continuation of application Ser. No. 10/281,011, filed Oct. 25, 2002 abandoned, which is a continuation of application Ser. No. 09/573,403, filed May 18, 2000 abandoned.

The present invention relates to the use of hydroxydiphenyl ether compounds as antimicrobially active substances, to certain new compounds of this type and to processes for the preparation of these compounds.

It is known that certain halogenated diphenyl ether compounds have an excellent antimicrobial activity. These compounds are therefore widely used, for example as active substances for the antimicrobial finishing of medical items and household articles, as detergent additive and in the hygiene sector, for example in soaps or dental hygiene products. Such halogenated compounds are described in DE 2538016. However it is desirable to be able to provide non-halogenated agents which are highly effective antimicrobial agents. Polymeric materials can be antimicrobially finished by incorporating halogenated diphenyl ether compounds, the active substances being, as a result of their excellent migration properties, constantly conveyed to the surface of the corresponding material ("slow release"). For certain industrial applications, this effect is undesired since the long-term effect of antimicrobially finished materials such as textiles, paper, plastics, cellulose sponges etc. is reduced at the same time.

The object of the present invention is thus to provide non-halogenated hydroxydiphenyl ether compounds for use as antimicrobially active substances and which, at the same time, are stable to migration.

The present invention provides the use of hydroxydiphenyl ether compounds of the following formula

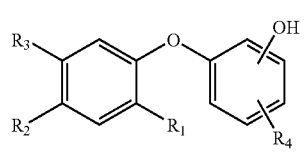

(1)

wherein when OH is in the para position with respect to the ether linkage $R_1$ and $R_2$ are independently of each other hydrogen, hydroxy, $C_1$–$C_{20}$alkyl, $C_5$–$C_7$cycloalkyl, $C_1$–$C_6$alkylcarbonyl, $C_1$–$C_{20}$alkoxy, phenyl or phenyl-$C_1$–$C_3$-alkyl;

$R_3$ is hydrogen, $C_1$–$C_{20}$alkyl or $C_1$–$C_{20}$alkoxy;

$R_4$ is hydrogen, $C_1$–$C_{20}$alkyl, hydroxy substituted $C_1$–$C_{20}$alkyl, $C_5$–$C_7$cycloalkyl, hydroxy, formyl, acetonyl, $C_1$–$C_6$alkylcarbonyl, $C_2$–$C_{20}$alkenyl, carboxy, carboxy$C_1$–$C_3$alkyl, $C_1$–$C_3$alkylcarbo-nyl$C_1$–$C_3$alkyl or carboxyallyl;

wherein when OH is in the meta position with respect to the ether linkage $R_2$ is hydrogen, $C_1$–$C_{20}$alkyl, hydroxy substituted $C_1$–$C_{20}$alkyl or $C_1$–$C_6$alkylcarbonyl;

$R_1$ and $R_3$ are independently of each other hydrogen, $C_1$–$C_6$alkylcarbonyl or $C_1$–$C_{20}$alkyl;

$R_4$ is hydrogen, $C_1$–$C_{20}$alkyl, hydroxy substituted $C_1$–$C_{20}$alkyl, $C_5$–$C_7$cycloalkyl, hydroxy, formyl, acetonyl, $C_1$–$C_6$alkylcarbonyl, $C_2$–$C_{20}$alkenyl, carboxy, carboxy$C_1$–$C_3$alkyl, $C_1$–$C_3$alkylcarbnyl$C_1$–$C_3$alkyl or carboxyallyl;

wherein when OH is in the ortho position with respect to the ether linkage $R_1$ is hydrogen, $C_1$–$C_6$alkyl carbonyl or $C_1$–$C_{20}$alkyl;

$R_4$ is hydrogen, $C_1$–$C_{20}$alkyl, hydroxy substituted $C_1$–$C_{20}$alkyl, $C_5$–$C_7$cycloalkyl, hydroxy, formyl, acetonyl, $C_1$–$C_6$alkylcarbonyl, $C_2$–$C_{20}$alkenyl, carboxy, carboxy$C_1$–$C_3$alkyl, $C_1$–$C_3$alkylcarbonyl$C_1$–$C_3$alkyl or carboxyallyl;

$R_2$ and $R_3$ are independently of each other hydrogen, $C_1$–$C_6$ alkyl carbonyl or $C_1$–$C_{20}$alkyl;

with the proviso that compounds wherein OH is in the para position with respect to the ether linkage and $R_1$ and $R_3$ are both hydrogen and $R_2$ is methoxy or methyl; or a compound wherein OH is in the para position with respect to the ether linkage $R_2$ is hydrogen, $R_1$ is isopropyl and $R_3$ is methyl are excluded; as antimicrobial agents.

$C_1$–$C_{20}$alkyl is straight-chain or branched alkyl radicals such as methyl, ethyl, n-propyl, isopropyl, n-butyl, sec-butyl, tert-butyl, pentyl, iso-pentyl, tert-pentyl, hexyl, cyclohexyl, heptyl, octyl, isooctyl, nonyl or decyl and the like.

$C_1$–$C_{20}$alkoxy is straight-chain or branched alkoxy radicals such as methoxy, ethoxy, n-propoxy, isopropoxy, n-butoxy, sec-butoxy, tert-butoxy, pentyloxy, iso-pentyloxy, tert-pentyloxy, heptyloxy, octyloxy, isooctyloxy, nonyloxy or decyloxy and the like.

$C_1$–$C_6$alkyl carbonyl is straight-chain or branched carbonyl radicals such as acetyl, propionyl, butyryl, isobutyryl, valeryl, isovaleryl or pivaloyl and the like.

Hydroxy substituted $C_1$–$C_{20}$alkyl is hydroxymethyl, hydroxyethyl, hydroxypropyl, hydroxybutyl, hydroxypentyl, hydroxyhexyl, hydroxyheptyl, hydroxyoctyl, hydroxynonyl or hydroxydecyl and the like.

Preferably compounds of formula (1) are used wherein, when OH is in the para position with respect to the ether linkage $R_1$ and $R_2$ are independently of each other hydrogen, $C_1$–$C_{20}$alkyl, $C_1$–$C_6$ alkyl carbonyl or $C_1$–$C_{20}$alkoxy;

$R_3$ is hydrogen, $C_1$–$C_{20}$alkyl or $C_1$–$C_{20}$alkoxy;

$R_4$ is hydrogen, $C_1$–$C_{20}$alkyl, hydroxy, formyl, acetonyl, allyl, carboxymethyl, carboxyallyl, hydroxy substituted $C_1$–$C_{20}$alkyl or $C_1$–$C_6$ alkyl carbonyl;

wherein when OH is in the meta position with respect to the ether linkage $R_2$ is hydrogen, $C_1$–$C_{20}$alkyl, hydroxy substituted $C_1$–$C_{20}$alkyl or $C_1$–$C_6$alkyl carbonyl;

$R_1$ and $R_3$ are independently of each other hydrogen, $C_1$–$C_6$alkyl carbonyl or $C_1$–$C_{20}$alkyl;

$R_4$ is hydrogen, $C_1$–$C_{20}$alkyl, hydroxy, formyl, acetonyl, allyl, carboxymethyl, carboxyallyl, hydroxy substituted $C_1$–$C_{20}$alkyl or $C_1$–$C_6$ alkyl carbonyl;

wherein when OH is in the ortho position with respect to the ether linkage $R_1$ is hydrogen, $C_1$–$C_6$ alkyl carbonyl or $C_1$–$C_{20}$alkyl;

$R_4$ is hydrogen, $C_1$–$C_{20}$alkyl, hydroxy, formyl, acetonyl, allyl, carboxymethyl, carboxyallyl, hydroxy substituted $C_1$–$C_{20}$alkyl or $C_1$–$C_6$ alkyl carbonyl;

$R_2$ and $R_3$ are independently of each other hydrogen, $C_1$–$C_6$ alkyl carbonyl or $C_1$–$C_{20}$alkyl;

with the proviso that compounds wherein OH is in the para position with respect to the ether linkage and $R_1$ and $R_3$ are both hydrogen and $R_2$ is methoxy or methyl; or a compound wherein OH is in the para position with respect to the ether linkage $R_2$ is hydrogen, $R_1$ is isopropyl and $R_3$ is methyl are excluded.

Another aspect of the invention are certain compounds described by formula (1) which are novel.

These novel compounds are of formula (1) wherein when OH is in the ortho position with respect to the ether linkage and $R_2$, $R_3$ and $R_4$ are hydrogen and $R_1$ is $C_1$–$C_{20}$alkyl.

Preferably these novel compounds are of formula (1) wherein when OH is in the ortho position with respect to the ether linkage and $R_2$, $R_3$ and $R_4$ are hydrogen and $R_1$ is $C_1$–$C_5$alkyl.

Compounds of particular interest include the following:

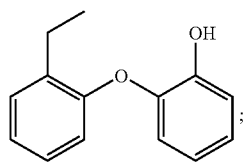

(2)

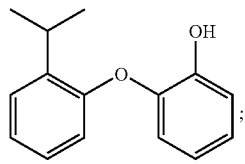

(3)

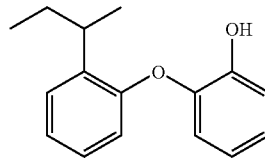

(4)

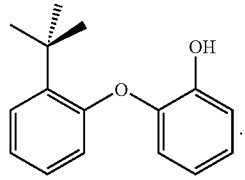

(5)

Further novel compounds are of formula (1) wherein when OH is in the meta position with respect to the ether linkage and $R_2$, $R_3$ and $R_4$ are hydrogen and $R_1$ is $C_1$–$C_{20}$alkyl.

Preferably these novel compounds are of formula (1) wherein when OH is in the meta position with respect to the ether linkage and $R_2$, $R_3$ and $R_4$ are hydrogen and $R_1$ is $C_1$–$C_5$ alkyl.

Compounds of particular interest include the following:

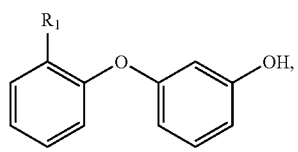

(6)

wherein
$R_1$ is $C_1$–$C_5$alkyl; for example the compound of formula

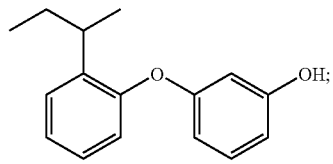

(6a)

or compounds of formula

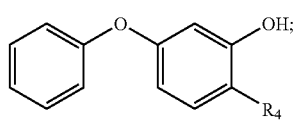

(7)

wherein
$R_4$ is $C_1$–$C_5$alkyl, for example the compound of formula

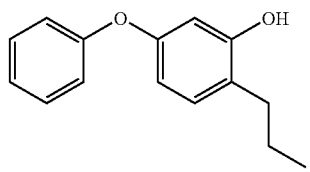

(7a)

Further novel compounds are of formula (1) wherein when OH is in the para position with respect to the ether linkage and $R_2$ and $R_4$ are hydrogen and $R_1$ and $R_3$ are $C_1$–$C_{20}$alkyl.

Preferably these novel compounds are of formula (1) wherein when OH is in the meta position with respect to the ether linkage and $R_2$ and $R_4$ are hydrogen and $R_1$ and $R_3$ are $C_1$–$C_5$ alkyl.

Compounds of particular interest include the following:

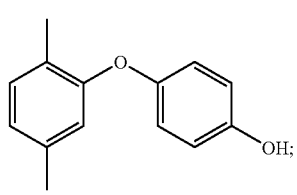

(8)

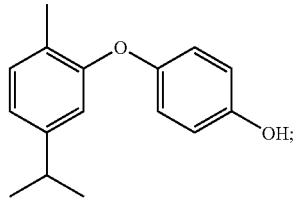

(9)

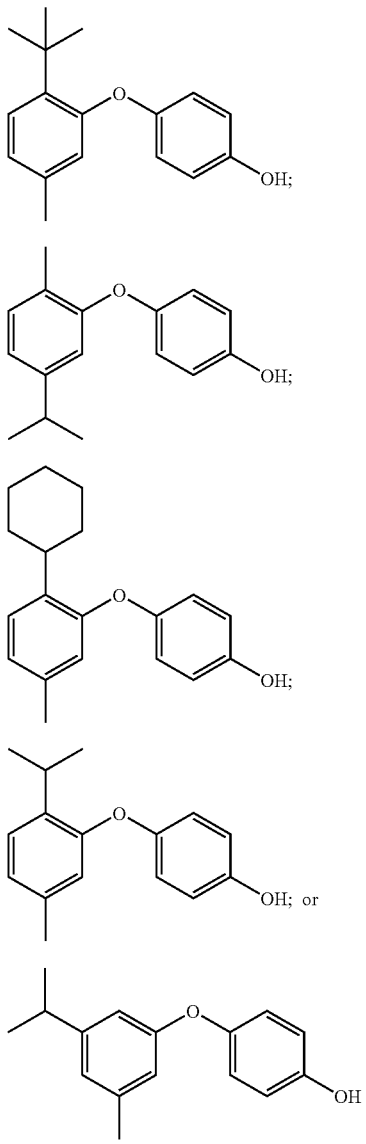

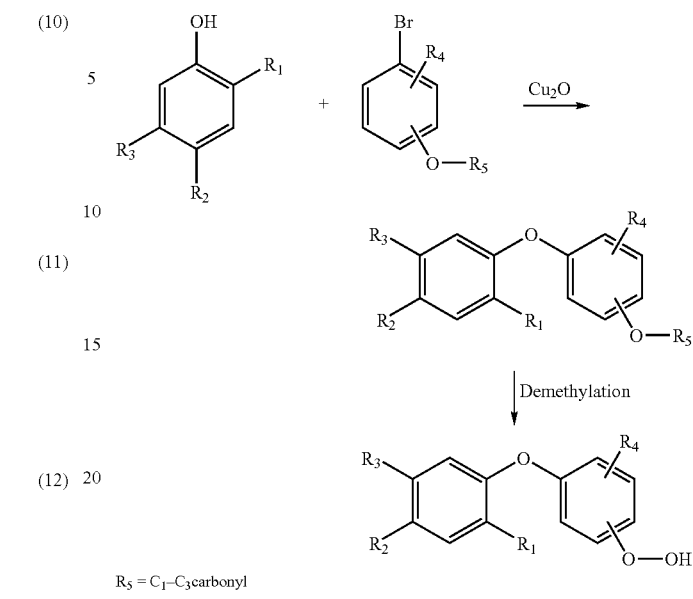

$R_5 = C_1-C_3$ carbonyl

Another aspect of the present invention is a process for the preparation of compounds of formula (1) wherein when OH is in the ortho position with respect to the ether linkage and $R_2$, $R_3$ and $R_4$ are hydrogen and $R_1$ is $C_1-C_{20}$alkyl, compounds of formula (1) wherein when OH is in the meta position with respect to the ether linkage and $R_2$, $R_3$ and $R_4$ are hydrogen and $R_1$ is $C_1-C_{20}$alkyl and compounds of formula (1) wherein when OH is in the para position with respect to the ether linkage and $R_2$ and $R_4$ are hydrogen and $R_1$ and $R_3$ are $C_1-C_{20}$alkyl.

The process comprises reacting a substituted phenol with an ether substituted halogenphenol in the presence of alkali and a catalytically active quantity of copper or of a copper compound, and the resulting alkyloxybenzol compound is then heated in the presence of hydrogen halide and acid in order to convert the alkyloxy group to a hydroxy group. An example of the reaction scheme is shown below, wherein R represents one of the groups $R_1$, $R_2$ or $R_3$.

Preferred combinations of reagents include $2-C_1-C_{20}$alkyl substituted phenols and 2-methoxy-bromophenol.

Other preferred combinations of reagents include $2-C_1-C_{20}$alkyl substituted phenols and 3-methoxy-bromophenol.

Other preferred combinations of reagents include 2,5-$C_1-C_{20}$dialkyl substituted phenols and 4-methoxy-bromophenol. Preferred bases are hydroxides/carbonates from group ½ metals.

The alkali required for the reaction can be added in different forms. For example the substituted phenol can be reacted in the form of alkali phenolate. It is also possible to introduce for example solid potassium hydrate into the mixture of phenol and halogenphenol, in which case homogeneity can be achieved by heating to 120 to 130° C. It is also possible to use aqueous alkali solutions and remove the water during the reaction, for example by azeotropic distillation in the presence of an organic entrailing agent.

The reaction may be also carried out in the presence of a solvent such as an aliphatic ether containing 6 or more carbon atoms and boiling at a temperature above 130° C. and also ethers of polyglycols such as di- and tri- ethylene gylcol and in high boiling solvents as Pyridin, DMF, DMA, DMSO, Toluene, Xylene etc.

General catalysts for Ullmann condensation are Cu, $Cu_2Cl_2$, bas. $CuCO_3$, $CuCl_2$, CuO or $Cu_2O$. Copper or copper compounds are used in known manner as catalysts for example in quantities of from 0.1 to 2.5% based on the halogenphenol. The reaction temperatures are generally from 150° C. to 200° C. whilst the reaction times vary from 1 to 16 hours. The reaction may be carried out under elevated pressure.

Suitable reagents used in the demethylation step include hydrogen bromide. Suitable acids used in the demethylation step include acetic acid. General reagents are $AlCl_3$, $BCl_3$, $BF_3$, HBr, HI, preferably pyridinium×HCl.

The reaction can be worked up in the usual way. Unreacted starting materials can be separated off by distillation, optionally under vacuum.

A further aspect of the invention includes other certain compounds described by formula (1) which are novel.

These novel compounds are of formula (1) wherein when OH is in the ortho position with respect to the ether linkage $R_1$, $R_2$ and $R_3$ are hydrogen;

$R_4$ is in the meta position with respect to the ether linkage and is $C_1$–$C_6$ alkyl carbonyl.

Compounds of particular interest include the following:

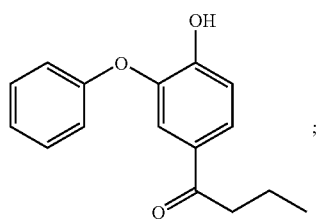
(15)

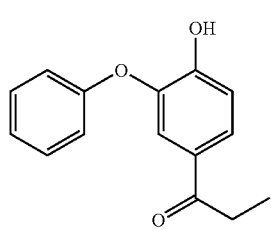
(16)

further novel compounds are of formula (1) wherein when OH is in the meta position with respect to the ether linkage and $R_1$, $R_2$ and $R_3$ are hydrogen and $R_4$ is in the para position with respect to the ether linkage and is $C_1$–$C_6$ alkyl carbonyl.

Compounds of particular interest include the following:

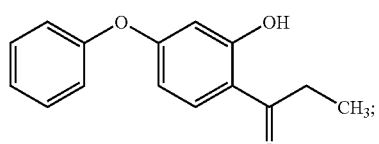
(17)

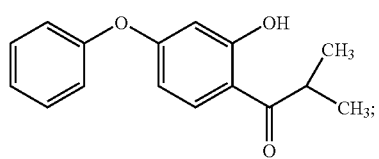
(18)

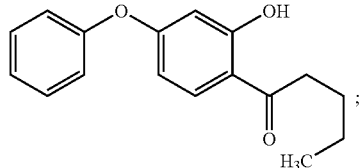
(19)

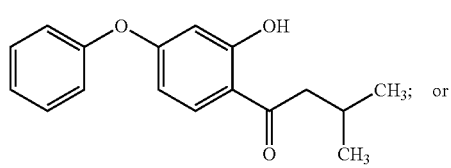
(20)

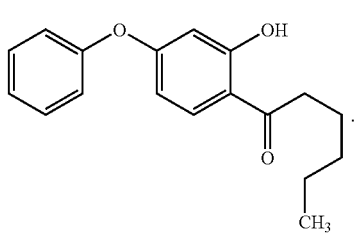
(21)

A further aspect of the present invention is another process for the preparation of compounds of formula (1) wherein when OH is in the meta position with respect to the ether linkage and $R_1$, $R_2$ and $R_3$ are hydrogen and $R_4$ is in the para position with respect to the ether linkage and is $C_1$–$C_6$ alkyl carbonyl and also for compounds of formula (1) wherein when OH is in the ortho position with respect to the ether linkage and $R_1$, $R_2$ and $R_3$ are hydrogen and $R_4$ is in the meta position with respect to the ether linkage and is $C_1$–$C_6$ alkyl carbonyl.

The process comprises reacting an acyl chloride with a phenoxyphenol, such as meta-phenoxyphenol or ortho-phenoxyphenol, in the presence of activated zinc at a temperature of between 70° C. to 80° C. The hydroxyl group undergoes acylation, as shown in the scheme below:

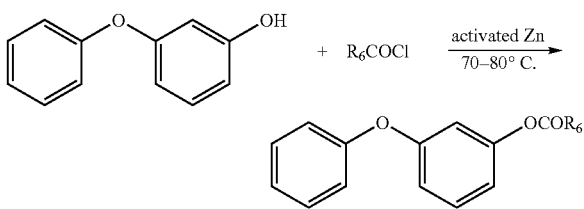

This acyl compound then undergoes a "Fries rearrangement" in the presence of aluminium chloride at a temperature of 145° C. to 150° C., producing an acylated phenol.

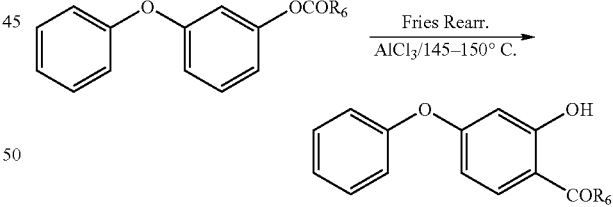

Preferably $R_6$ is $C_1$–$C_6$ alkylcarbonyl.

These compounds may also be amenable by direct acylation of phenols with catalysts such as Lewis acids as $AlCl_3$, $ZnCl_2$, $FeCl_3$, $BCl_3$, $BF_3$, transition metal trifluorosulfonates (eg. $Sc(OTf)_3$) in inert solvents as EDC, $CH_2Cl_2$, $CS_2$ or nitrobenzene.

Further novel compounds are of formula (1) wherein when OH is in the meta position with respect to the ether linkage and $R_1$, $R_2$ and $R_3$ are hydrogen and $R_4$ is in the para position with respect to the ether linkage and is $C_1$–$C_{20}$ alkyl.

Preferably these novel compounds are of formula (1) wherein when OH is in the meta position with respect to the ether linkage $R_1$, $R_2$ and $R_3$ are hydrogen;
$R_4$ is in the para position with respect to the ether linkage and is $C_1$–$C_5$alkyl.

Compounds of particular interest include the following:

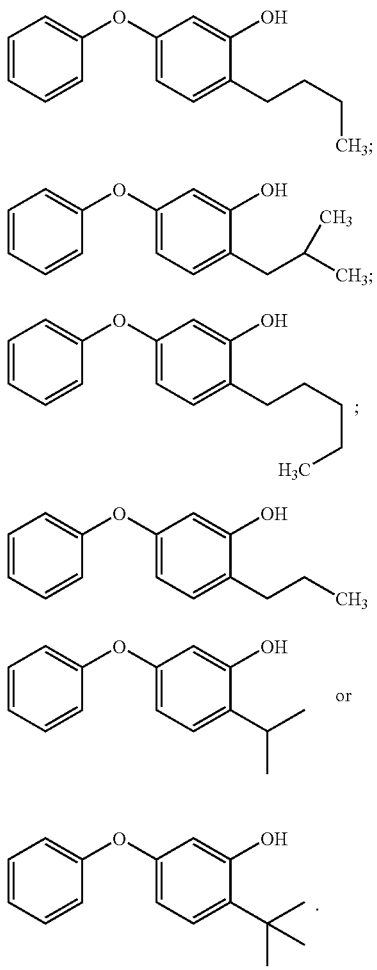

(22)

(23)

(24)

(25)

(26)

(27)

A further aspect of the present invention is another process for the preparation of compounds of formula (1) wherein when OH is in the meta position with respect to the ether linkage and $R_1$, $R_2$ and $R_3$ are hydrogen and $R_4$ is in the para position with respect to the ether linkage and is $C_1$–$C_{20}$alkyl.

The process comprises reacting an acyl chloride with meta-phenoxyphenol in the presence of activated zinc at a temperature of between 70° C. to 80° C. The hydroxyl group undergoes acylation, as shown in the scheme below:

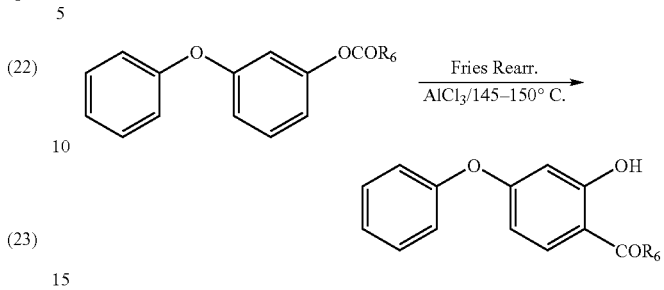

This acyl compound then undergoes a "Fries rearrangement" in the presence of aluminium chloride at a temperature of 145° C. to 150° C., producing an acylated phenol.

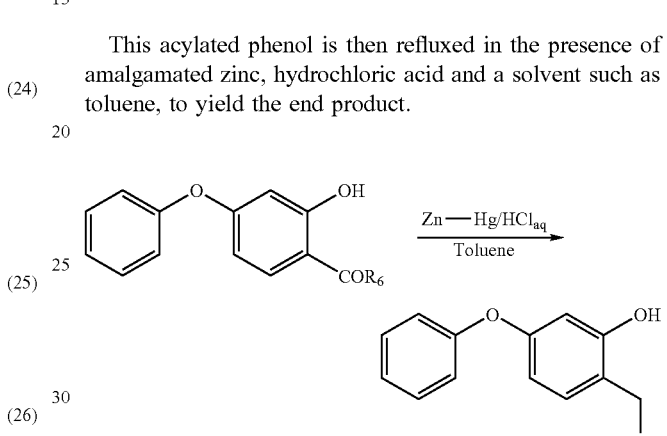

This acylated phenol is then refluxed in the presence of amalgamated zinc, hydrochloric acid and a solvent such as toluene, to yield the end product.

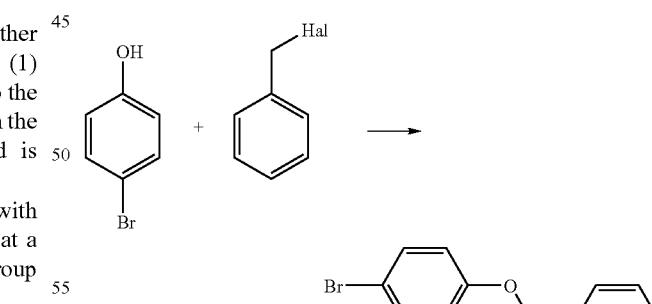

$R_6$ is $C_1$–$C_{19}$alkyl.

Reduction to these compounds is also achieved by catalytic hydrogenation.

Alternatively, compounds of formula (1) wherein the hydroxy group is in para position with respect to the ether linkage can be obtained by the "benzylic ether route" according to the following reaction scheme:

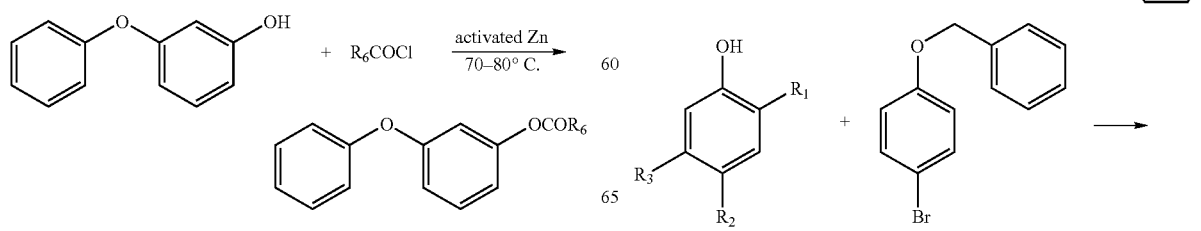

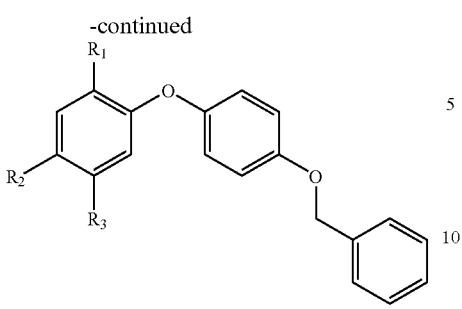

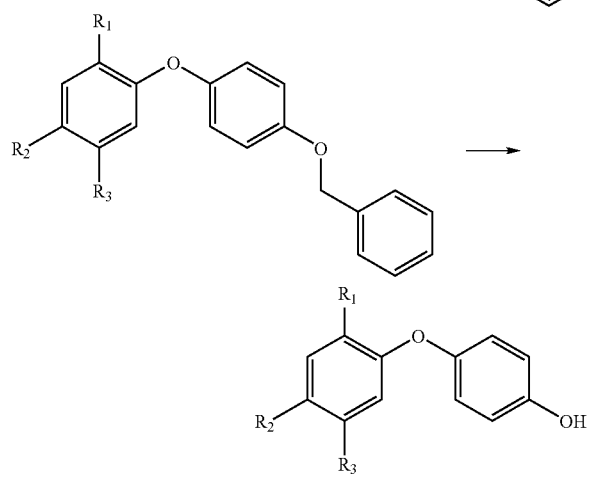

This is basically the same synthesis route as described above but it's applying the benzylic ether of p-bromo phenol instead of the methyl ether.

The following ether compounds can also be employed:

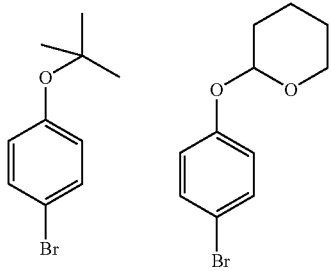

The hydroxydiphenyl ether compounds according to the invention are thermally stable and antimicrobially effective compounds of low volatility and having a severely reduced tendency to migrate. They are therefore suitable for the antimicrobial finishing of polymeric compounds, for example in plastics, rubbers, paints, surface coatings, (textile) fibres which are exposed to a microbially contaminated environment.

Examples of polymers and other substrates which can be antimicrobially finished in this way are:
polymers of mono- and diolefins,
polyolefins,
copolymers of mono- and diolefins with one another or with other vinyl monomers,
hydrocarbon resins,
polystyrene,
copolymers of styrene or α-methylstyrene or dienes or acrylic derivatives,
graft copolymers of styrene or α-methylstyrene.
halogen-containing polymers,
polymers derived from α,β-unsaturated acids and derivatives thereof, such as polyacrylates and polymethacrylates,
polymers derived from unsaturated alcohols and amines or acyl derivatives or acetals thereof,
homo- and copolymers of cyclic ethers, polyacetals, polyphenylene oxides and polyphenylene sulfides and mixtures thereof with styrene polymers or polyamides,
polyurethanes derived from polyethers, polyesters and polybutadienes having terminal hydroxyl groups on the one hand and aliphatic or aromatic polyisocyanates on the other, and precursors thereof,
polyamides and copolyamides derived from diamines and dicarboxylic acids and/or from aminocarboxylic acids or the corresponding lactams,
polyureas, polyimides, polyamide-imides, polyetherimides, polyesterimides, polyhydantoins and polybenzimidazoles,
polyesters,
polycarbonates and polyester carbonates,
polysulfones, polyether sulfones and polyether ketones,
crosslinked polymers derived from aldehydes on the one hand and phenols, urea or melamine on the other hand, such as phenol-formaldehyde resins, urea-formaldehyde resins and melamine-formaldehyde resins,
drying and non-drying alkyd resins,
unsaturated polyester resins,
crosslinkable acrylic resins,
alkyd resins, polyester resins and acrylate resins,
crosslinked epoxy resins,
superabsorbent polymers
natural polymers, such as cellulose, natural rubber, gelatine, and derivatives thereof modified chemically in a polymer-homologous manner, such as cellulose acetates, cellulose propionates cellulose butyrates, or the cellulose ethers, such as methylcellulose; and also rosins and derivatives.

The invention thus also provides a composition comprising
(A) an organic material to be antimicrobially finished and
(B) a compound of the formula (1).

The invention also relates to a process for the antimicrobial finishing of an organic material, which comprises adding at least one compound of the formula (1) thereto, and to the use of the compound of the formula (1) for the antimicrobial finishing of polymeric materials.

The amount of antimicrobial active substance to be used depends on the organic material to be antimicrobially finished and on the intended use of the material finished in this way. The composition according to the invention generally comprises, per 100 parts by weight of component (A), from 0.01 to 15 parts by weight, in particular from 0.05 to 10 parts by weight, and especially from 0.1 to 5 parts by weight of the antimicrobial active substance (component (B)).

The antimicrobial active substance (component (B)) can also be a mixture of two or more compounds of the formula (1). The compositions according to the invention can, in addition to the compounds according to the invention, also comprise other additives, for example antioxidants or light protection agents.

Incorporation into the organic polymers, for example into the synthetic organic, in particular thermoplastic, polymers can take place by adding the hydroxydiphenyl ether compound according to the invention and, if desired, other additives by the methods customary in the art. Incorporation can expediently take place before or during shaping, for example by mixing the pulverulent components or by adding the antimicrobial active substance to the melt or solution of the polymer, or by applying the dissolved or dispersed compounds to the polymer, if desired with subsequent evaporation of the solvent. Another method of incorporating the mixtures according to the invention into polymers involves adding the former before or during polymerization of the corresponding monomers or before crosslinking.

The mixtures according to the invention can also be added to the organic polymers to be finished in the form of a masterbatch which comprises these compounds, for example, in a concentration of from 2.5 to 25% by weight.

The resulting antimicrobially finished polymer compositions can be converted into shaped articles, for example fibres, films, tapes, sheets, multi-wall sheets, containers, tubes and other profiles, by conventional methods, for example by hot pressing, spinning, extrusion or injection moulding.

The hydroxydiphenyl ether compounds of the formula (1) are also suitable for the antimicrobial finishing of undyed and dyed or printed fibre materials made, for example, of silk, wool, polyamide, polyester or polyurethane, and in particular of cellulosic fibre materials of all types. Examples of such fibre materials are the natural cellulose fibres, such as cotton, linen, jute and hemp, and also pulp and regenerated cellulose. The hydroxydiphenyl ether compounds according to the invention are also suitable for the antimicrobial finishing of hydroxyl-group-containing fibres which are present in mixed fabrics, for example, of mixtures of cotton with polyester fibres or polyamide fibres. The hydroxydiphenyl ether compounds of the formula (1) are also suitable for incorporation into non-wovens.

"Non-woven" is a type of fabric that is not spun and woven into a cloth, but instead bonded together. According to the ISO definition it is a manufactured sheet, web, or batt of directionally or randomly orientated fibres, bonded by friction, and/or adhesion.

Nonwoven textiles are widely used in disposable as well as durable goods, such as, baby diaper, feminine hygiene, adult incontinence, wipers, bed linings, automotive industries, medical face masks, air and water filtration, home furnishing and geotextiles. Such materials can be fabricated by different techniques, such as spunbonding, melt blown, carded thermal bonding and carded chemical bonding, dry and/or wet laid and needlefelts. Because of the nature of such applications, increasingly the market is demanding products with specific properties such as antimicrobial efficacy.

For this purpose, one or more compounds of the formula (1) are advantageously applied to the textile fibre material in an amount of from 0.01 to 20% by weight, preferably 0.1–3% by weight, and in particular from 0.25 to 2% by weight, based on the weight of the fibre material, in a process analogous to dyeing.

The hydroxydiphenyl ether compounds according to the invention can be applied to the fibre material and fixed to the fibre in different ways, in particular in the form of aqueous dispersions or printing pastes.

The textile fibre materials finished using the compounds of the formula (1) according to the invention have an excellent and long-lasting antimicrobial protection.

An antimicrobial textile treatment formulation has, for example, the following composition:
20% by weight of a compound of formula (1)
5% by weight of sodium lauryl sulfate
10% by weight of an ethoxylated fatty alcohol
40% by weight of propylene glycol and
25% by weight of water.

The hydroxydiphenyl ether compounds according to the invention can be also be used in paper finishing, printing thickeners containing starch, varnishes and paints. The hydroxydiphenyl ether compounds according to the invention are also useful for the disinfection and general antimicrobial treatment, such as deodorising, of the skin, mucous membrane and hair, preferably for the disinfection of hands and wounds. The hydroxydiphenyl ether compounds according to the invention are useful for the preservation of cosmetic and household products against microbial spoilage.

Therefore, these compounds are suitable as an antimicrobial active substance in personal care products as shampoos, bath- and shower additives, hair-care products, liquid and bar soaps, lotions and cremes, deodorants, other aqueous or alcoholic solutions, for example cleaning solutions for the skin, moist cleaning sheets, oils and powders.

A further subject of the present invention is therefore a personal care composition comprising at least one compound of the formula (1) and cosmetically tolerable carriers or auxiliaries.

The personal care composition according to the present invention comprises 0.01 to 15, preferably 0.5 to 10% b.w. of the hydroxydiphenyl ether compounds of formula (1) and cosmetically tolerable carriers or auxiliaries.

The personal care composition according to the invention can be formulated as a water-in-oil or oil-in-water emulsion, as an oil-in-alcohol lotion, as a vesicular dispersion of an ionic or non-ionic amphiphilic lipid, as a gel, solid stick, aerosol formulation or a surfactant based formulation, such as a soap or skin cleanser.

As a water-in-oil or oil-in-water emulsion, the cosmetically compatible auxiliary preferably contains 5 to 50% of an oil phase, 5 to 20% of an emulsifier and 30 to 90% of water. The oil phase can in this case contain any oil suitable for cosmetic formulations, e.g. one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

Any conventionally usable emulsifier can be used for the cosmetic composition according to the invention, for example one or more ethoxylated esters of natural derivatives, e.g. poly-ethoxylated esters of hydrogenated castor oil; or a silicone oil emulsifier, e.g. a silicone polyol; an optionally ethoxylated fatty acid soap; an ethoxylated fatty alcohol; an optionally ethoxylated sorbitan ester; an ethoxylated fatty acid; or an ethoxylated glyceride.

The cosmetic composition may also comprise further components; e.g. emollients, emulsion stabilisers, skin humectants, skin tanning accelerators, thickeners, such as xanthan, moisture-retention agents, such as glycerol, preservatives, perfumes and colourings.

The preparation of the cosmetic composition can be effected by physically mixing the antimicrobial(s) with the auxiliary by customary methods, for example by simply stirring the individual components together.

Cosmetic formulations include a very wide range of cosmetic products. Suitable products are, for example, especially the following:
skin-care products, for example skin washing and cleansing products in the form of bars of soap or liquid soaps, syndets or washing pastes,
bath products, for example liquid (foam baths, milks, shower products) or solid bath products, such as bath pearls and bath salts;

skin-care products, such as skin emulsions, multiple emulsions or skin oils;

decorative body-care products, for example face make-ups in the form of day or powder creams, face powders (lose and compressed), rouge or cream make-ups, eye-care products, for example eye shadow products, mascara, eyeliners, eye creams or eye-fix creams; lip-care products, for example lipstick, lip gloss, lip liner, nail-care products, such as nail varnish, nail varnish remover, nail hardeners or cuticle removers;

feminine hygiene products, such as feminine hygiene washing lotions or sprays;

foot-care products, for example foot baths, foot powders, food creams or foot balms, special deodorants and antiperspirants or products for scrubbing off callouses;

sunscreens, such as sun milks, lotions, creams, oils, sunblockers or tropicals, pre-sun products or after-sun products;

suntanning products, for example self-tanning creams;

depigmenting products, for example products for bleaching or lightening skin;

insect repellents, for example insect oils, lotions, sprays or sticks;

deodorants, for example deodorant sprays, non-aerosol sprays, deodorant gels, sticks or roll-ons;

antiperspirants, for example antiperspirant sticks, creams or roll-ons;

products for cleansing and treating impure skin, for example syndets (solid or liquid), peeling or scrubbing products or peeling masks;

chemical depilatory products, for example depilatory powders, liquid depilatory products, creamy or pasty depilatory products, depilatory gels or aerosol foams;

shaving products, for example shaving soap, foaming shaving creams, non-foaming shaving creams, shaving foams and gels, preshaving products for dry shaving, aftershaves or aftershave lotions;

scents, for example perfumes (Eau de Cologne, Eau de Toilette, Eau de Parfum, Parfum de Toilette, perfume), perfume oils or perfume creams;

products for oral and dental hygiene as well as for dentures, for example toothpastes, tooth gels, tooth powders, mouth-wash concentrates, anti-plaque mouth-washes, denture cleaning products or denture adhesion products;

cosmetic formulations for hair treatment, for example hair washes in the form of shampoos, hair conditioners, hair-care products, for example pretreatment products, hair tonics, hair styling creams and gels, pomades, hair rinses, deep conditioning treatments, intensive hair care treatments, hair setting products, for example waving agents for perms (hot wave, mild wave, cold wave), hair straightening products, liquid hair fixatives, hair foams, hair sprays, bleaching agents, for example hydrogen peroxide solutions, bleaching shampoos, bleaching creams, bleaching powders, bleaching pastes or oils, temporary, semitemporary or permanent hair dyes, products containing self-oxidising dyes, or natural hair dyes, such as henna or camomile.

An antimicrobial soap has, for example, the following composition:
0.01 to 5% by weight of a compound of the formula (1)
0.3 to 1% by weight of titanium dioxide
1 to 10% by weight of stearic acid to 100% of soap base, for example the sodium salts of tallow fatty and coconut fatty acid or glycerols.

A shampoo has, for example, the following composition:
0.01 to 5% by weight of a compound of the formula (1)
12.0%, by weight of sodium laureth-2-sulfate,
4.0% by weight of cocamidopropylbetaine,
3.0% by weight of NaCl and
water to 100%.

A deodorant has, for example, the following composition:
0.01 to 5% by weight of a compound of the formula (1)
60% by weight of ethanol,
0.3% by weight of perfume oil and
water to 100%.

The personal care formulations listed above can be in a very wide range of forms of presentation, for example
in the form of liquid formulations as an O/W emulsion,
in the form of a gel,
in the form of an oil, cream, milk or lotion,
in the form of a powder, lacquer, pellets or make-up,
in the form of a stick,
in the form of a spray (spray with propellant or pumping spray) or an aerosol,
in the form of a foam, or
in the form of a paste.

The oral hygiene composition may comprise an additional antibacterial enhancing agent, for example an anionic polymeric polycarboxylate, a dehydrated polyphosphate salt, a compound which provides a source of fluoride ions, a polishing material, including siliceous material or sodium bicarbonate, an orally acceptable vehicle, including a water-phase with humectant, thickeners, surface-active agents and a flavoring or sweetening-material.

The oral hygiene composition according to the invention contains from 0.003 to 5% by weight based on the total weight of the composition, of antimicrobial or a mixture of antimicrobials.

The preparation of the oral hygiene composition can be effected by physically mixing the antimicrobial(s) with the other ingredients by customary methods, for example by simply stirring the individual components together, then mixing further under vacuum.

An oral care formulation has, for example, the following composition:
10% by weight of Sorbitol,
10% by weight of Glycerin,
15% by weight of Ethanol,
15% by weight of Propylene gylcol,
0.5% by weight of Sodium lauryl sulfate,
0.25% by weight of Sodium methyl cocyl taurate,
0.25% by weight of Poloxypropylene/polyoxyethylene block copolymer,
0.10% by weight of Mint flavor,
0.3% by weight of a compound of formula (1),
48.6% by weight of water.

The oral hygiene composition may be in various forms of presentation including the form of a gel, paste, cream or mouthwash.

Furthermore the hydroxydiphenyl ether compounds according to the invention are useful as household cleaners for the cleaning and disinfection of hard surfaces.

A detergent has, for example, the following composition:
0.01 to 5% by weight of a compound of the formula (1)
3.0% by weight of Octanol 4EO,
1.3% by weight Fatty alcohol $C_8$–$C_{10}$ Polyglucoside,
3.0% by weight Isopropanol,
water to 100%.

A better understanding of the present invention and of its many advantages will be had by referring to the following Examples, given by way of illustration.

EXAMPLE 1

Reaction scheme first reaction step:

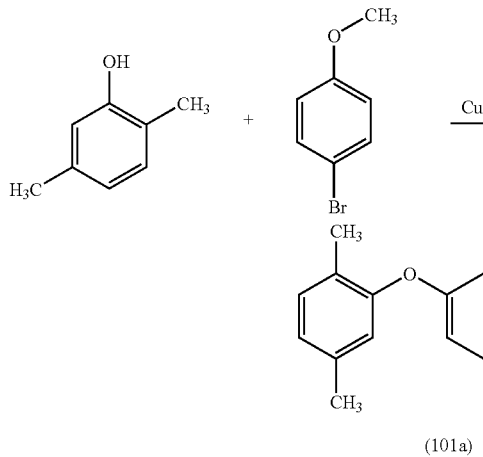

(101a)

The mixture of 6.1 g (0.05 mol) 2,5-Dimethylphenol, 2.8 g (0.05 mol) KOH, 0.4 g (0.006 mol) copper powder and 50 g (0.25 mol) bromo anisole is heated in a standard reaction apparatus, equipped with a water trap, to 160° C. for 5 h. After cooling the reaction mass is suspended in toluene and filtrated. After distilling off the solvent and excess reagent the product of formula (101a) is isolated by distillation at 125° C./0.01 mbar. A colourless oil is obtained, slowly crystallizing at room temperature. Yield: 4.6 g (40%)

Reaction scheme second reaction step:

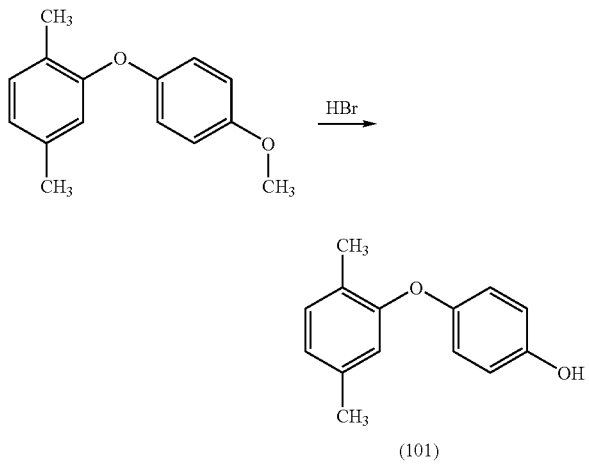

(101)

4.6 g (0.02 mol) of 4-(2,5-Dimethylphenoxy)-methoxy-benzol and 30 ml HBr (47% solution in water) are heated to reflux in 100 ml acetic acid for 4 h. After cooling and distilling off acetic acid the reaction mass is dissolved in 100 ml methylene chloride and washed with 200 ml water with pH adjusted to pH 10 with 10% NaOH. Product of formula (101) is isolated from the organic phase by distillation at 160° C./0.01 mbar. Yield: 2.2 g (52%)

EXAMPLE 2

Reaction scheme first reaction step:

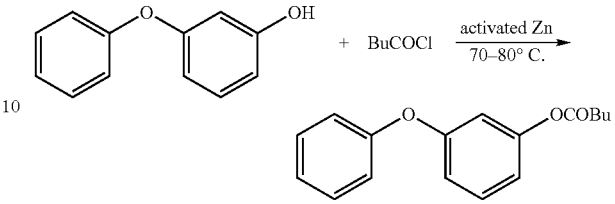

Into a three necked flask equipped with overhead stirrer & condenser was charged Acid chloride [57.25 m.moles], Toluene [250 ml] & activated zinc [57.24 m.moles]. This mixture stirred at room temperature [30° C.], for 15 minutes. m-Phenoxyphenol [4.5 g. 24.20 m.moles] in Toluene [150 ml], was added and the reaction mixture stirred at 70–75° C. for 30 minutes. TLC showed the absence of starting material. Reaction mixture cooled to room temperature & filtered. Organic layer washed with 2×100 ml of aqueous solution [20%] of Potassium carbonate followed by water wash. It was briefly drided over anhydrous sodiumsulphate and solvent distilled under reduced pressure to get O-Acyl compound. Yield 85%.

Reaction scheme second reaction step:

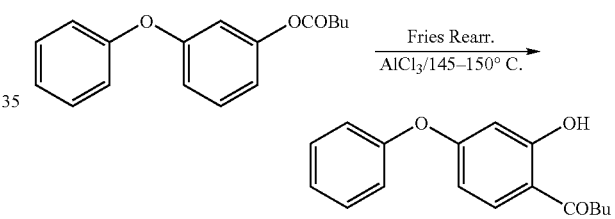

O-Acetate [16 m.moles], Aluminium chloride [20 m.moles], were mixed together and heated to 145–50° C. for 3 to 4 hrs. protected from moisture. TLC after 4hrs showed the absence of starting material. Reaction mixture was cooled to room temperature and poured to dil. hydrochloric acid and extracted with 2×50 ml of dichloromethane. Organic extract washed with water until the washings are neutral to litmus. Solvent distilled off and the residue chromatographed over silicagel using hexane:ethylacetate [98:2] as eluent. Yield of 2-Acylphenol is 72%.

Reaction scheme third reaction step:

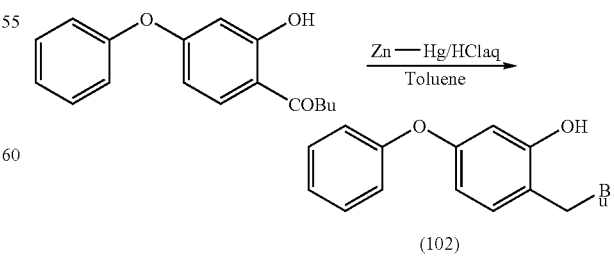

(102)

Amalgamated Zinc [12 g], prepared according to standard procedures was transferred to a three necked round bottomed flask provided with a over head stirrer and a reflux condenser. Water [10 ml], Conc.Hydrochloric acid [20 ml] were added followed by 2-Acyl phenol [10 m.moles] dissolved in 20 ml toluene. Ethanol [2 ml], was added the reaction mixture stirred and refluxed. Conc.Hydrochloric acid [3 to 4 ml], was added after every 3–4hrs of reflux. Heating stopped after 24 hrs of reflux. [TLC after 24 hrs of reflux indicated the presence of Starting material. Addition of further quantity of Zinc amalgam did not help]. Oraganic material extracted with 2×35 ml toluene and the extracts washed with water until washings neutral to litmus. Solvent distilled off under reduced pressure and the residue chromatographed over silicagel, using Hexane: Ethylacetate [97:3] as the eluent, to obtain the pure product of formula (102). Yield, 50–55%.

EXAMPLE 3

An agar incorporation test is carried out to determine the MIC of various compounds shown in table 1
Medium:
Nutrient agar as test agar for bacteria:
Mueller hinton agar to cultivate the aerobic bacteria
Mueller hinton bouillon for obtaining the suspension of microorganisms
Ethanol as solvent
Wilkins-Chalgren agar to cultivate the aerobic bacteria
Sabouraud glucose agar to cultivate the dermatophytes
Examples of Test bacteria
*Staphylococcus aureus* ATCC 6538
*Staphylococcus hominis* DSM 20330
*Escherichia coli* NCTC 8196
*Pseudomonas aeruginosa* CIP A-22
*Candida albicans* ATCC 10231
*Aspergillus niger* ATCC 6275

Procedure: The test substances are dissolved in ethanol, and a dilution series of the compound of the formula (102) in agar are prepared.

Anaerobic bacteria and dermatophytes are activated on agar-plates, and washes off with Mueller-Hinton bouillon. Aerobic bacteria are activated in Mueller-Hinton bouillon overnight. The test germ suspension are diluted with Mueller-Hinton bouillon to a density of McFarland standard 0.5.

10 µl of each germ suspension is dropped onto the agar plates containing the test substance, and the plates are then incubated at 37° C. for 2 days. (Aerobic bacteria are incubated at 36° C. for 72 hours, anaerobic bacteria are incubated at 30° C. for 72 hours). As controls, the bacterial suspensions are applied to agar plates without test substances. In order to exclude the solvent ethanol having an influence on the growth properties, the bacterial suspensions are applied to agar plates containing ethanol, but without test substance.

After the plates have been incubated, the growth of the bacteria on the test-substance-containing plates is compared with that on the control plates.

The minimum inhibitory concentration (MIC) is given as the lowest concentration which shows clear inhibition compared with the control.

The MIC values are given in the table 1 below.

TABLE 1

| Comp. of formula | Structure | Minimum Inhibitory Concentration [ppm] Test Organism | | | | | |
| --- | --- | --- | --- | --- | --- | --- | --- |
| | | SH | EC | CA | AN | SA | PA |
| (103) | | 30 | 30 | 30 | 120 | | |
| (104) | | 30 | 30 | 30 | 60 | | |
| (105) | | 30 | 30 | 30 | 30 | | |
| (106) | | 30 | 30 | 60 | 60 | | |

TABLE 1-continued
Minimum Inhibitory Concentration [ppm]
| Comp. of formula | Structure | Test Organism | | | | | |
|---|---|---|---|---|---|---|---|
| | | SH | EC | CA | AN | SA | PA |
| (107) | 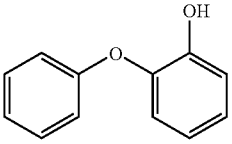 | 30 | 30 | 0 | 120 | | |
| (108) | 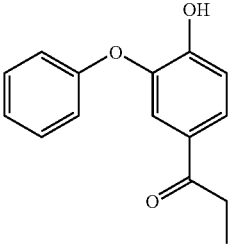 | 60 | 120 | 0 | 0 | | |
| (109) | 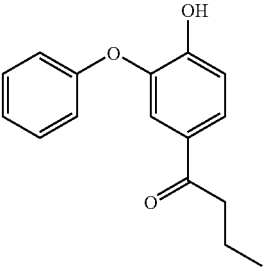 | 30 | 30 | 120 | 120 | | |
| (110) | 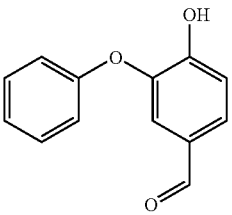 | 0 | 30 | 0 | 0 | | |
| (111) | 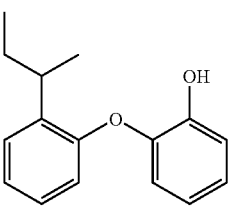 | 60 | 0 | 30 | 120 | | |
| (112) | 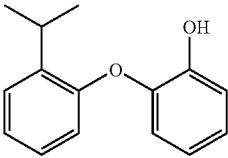 | 60 | 0 | 60 | 120 | | |
| (113) | 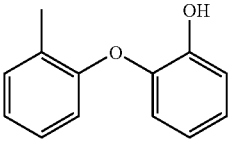 | 30 | 30 | 120 | 60 | | |

TABLE 1-continued

Minimum Inhibitory Concentration [ppm]

| Comp. of formula | Structure | Test Organism ||||||
|---|---|---|---|---|---|---|---|
| | | SH | EC | CA | AN | SA | PA |
| (114) | 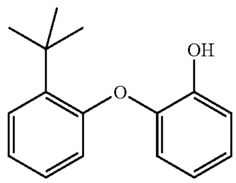 | 30 | 30 | 60 | 120 | | |
| (115) | 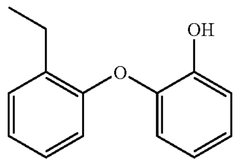 | 120 | 120 | 120 | 120 | | |
| (116) | 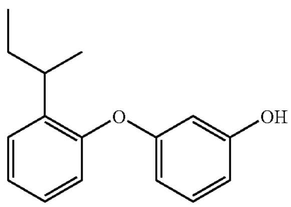 | 30 | 0 | 30 | 30 | | |
| (117) | 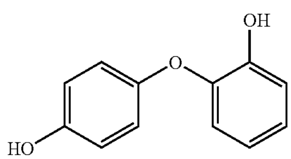 | 0 | 60 | 0 | | | 0 |
| (118) | 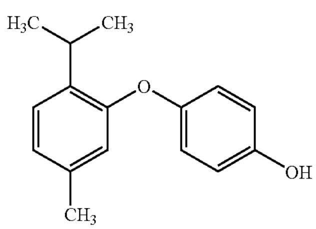 | 3 | 50 | 50 | | 5 | 0 |
| (119) | 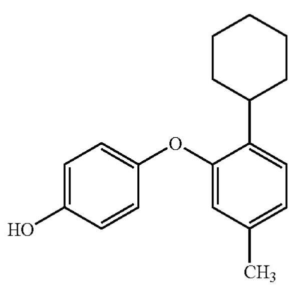 | 3 | 0 | 0 | | 3 | 0 |
| (120) | 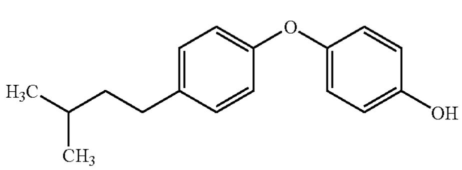 | 4 | 0 | 0 | | | 0 |

TABLE 1-continued

| Comp. of formula | Structure | Minimum Inhibitory Concentration [ppm] Test Organism | | | | | |
|---|---|---|---|---|---|---|---|
| | | SH | EC | CA | AN | SA | PA |
| (121) | | 5 | 0 | 13 | | 7 | 0 |
| (122) | | 6 | 0 | 13 | | 6 | 0 |
| (123) | | 8 | 0 | 0 | | | 0 |
| (124) | | 8 | 0 | 60 | | | 0 |
| (125) | | 30 | 120 | 30 | | | 0 |
| (103) | | 30 | 0 | 60 | | | 0 |
| (126) | | 120 | 120 | 120 | | | 0 |

TABLE 1-continued

Minimum Inhibitory Concentration [ppm]

| Comp. of formula | Structure | SH | EC | CA | AN | SA | PA |
|---|---|---|---|---|---|---|---|
| (127) | 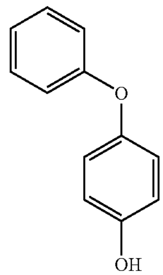 | | 100 | 50 | | 500 | 50 |
| (128) | 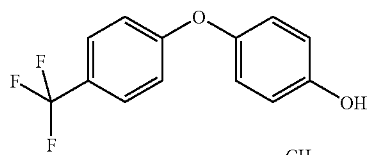 | | 50 | 50 | | 50 | 50 |
| (129) | 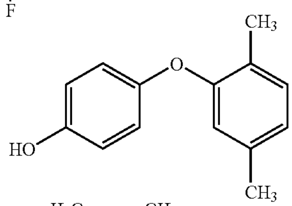 | | 0 | 25 | | 50 | 25 |
| (130) | 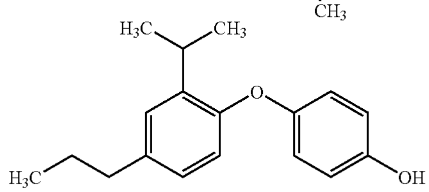 | | 0 | 20 | | 50 | 20 |

SA = *Staphylococcus aureus* ATCC 6538
SH = *Staphylococcus hominis* DSM 20328
EC = *Escherichia coli* NCTC 8196
PA = *Pseudomonas aeruginosa* CIP A-22
CA = *Candida albicans* ATCC 10231
AN = *Aspergillus niger* ATCC 6275

The results in the above table clearly show that the compounds have antimicrobial activity.

EXAMPLE 4

Preparation of Specific Diphenlyeter Compounds

The following compounds listed in table 2 are prepared by the methods described in detail below:

TABLE 2

| Comp. of form. | Structure | Name/CAS | Synthetic procedure-employed | MP [° C.] | Technique used for structure assignment |
|---|---|---|---|---|---|
| (107) | 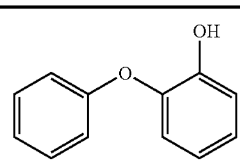 | 2-Phenoxyphenol 2417-10-9 | Procedure I & IV | 98 | 1. $^1$H-NMR 2. M.S. |

TABLE 2-continued

| Comp. of form. | Structure | Name/CAS | Synthetic procedure-employed | MP [° C.] | Technique used for structure assignment |
|---|---|---|---|---|---|
| (113) | 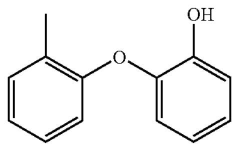 | 2-(2-Methyl)phenoxyphenol 26321-31-3 | Procedure I & IV | — | 1. $^1$H-NMR 2. M.S. |
| (115) | 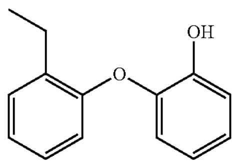 | 2-(2-Ethyl)phenoxyphenol 137610-67-4 | Procedure I & IV | — | 1. $^1$H-NMR 2. M.S. |
| (112) | 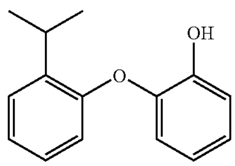 | 2-(2-Isopropyl)-phenoxyphenol. | Procedure I & IV | — | 1. $^1$H-NMR 2. M.S. |
| (111) | 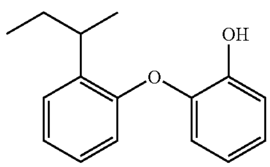 | 2-(2-sec-Butyl)-phenoxyphenol | Procedure I & IV | — | 1. $^1$H-NMR 2. M.S. |
| (114) | 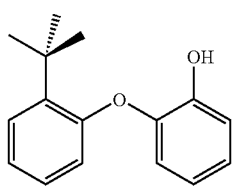 | 2-(2-tert-Butyl)-phenoxyphenol | Procedure I & IV | — | 1. $^1$H-NMR 2. M.S. |
| (131) | 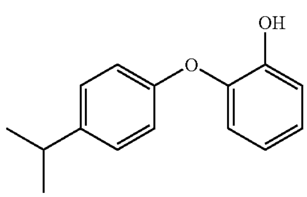 | 2-(4-Isopropyl)-phenoxyphenol | Procedure I & IV | — | 1. $^1$H-NMR 2. M.S. |
| (117) | 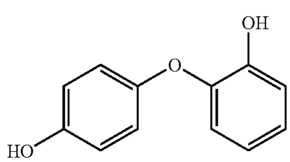 | 2-(4-Hydroxy phenoxy)phenol. 23990-90-1 | Procedure I & IV | 155 | 1. $^1$H-NMR 2. M.S. |
| (110) | 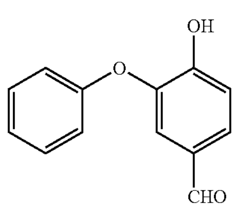 | 4-Hydroxy-3-phenoxy-benzaldehyde | Procedure I & IV | 118–120 | 1. $^1$H-NMR 2. M.S. |

TABLE 2-continued

| Comp. of form. | Structure | Name/CAS | Synthetic procedure-employed | MP [° C.] | Technique used for structure assignment |
|---|---|---|---|---|---|
| (109) | 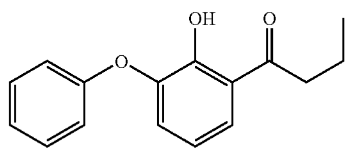 | 2-Butanoyl-6-phenoxyphenol | Procedure I, IV & VI A. | — | 1. $^1$H-NMR 2. M.S. |
| | | 4-Butanoyl-6-phenoxyphenol. | | | |
| (108) | 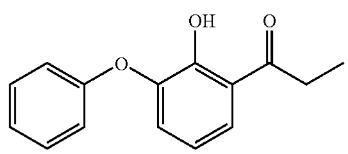 | 2-Propanoyl-6-phenoxyphenol | Procedure I, IV & VI A. | 94–97 | 1. $^1$H-NMR 2. M.S. |
| | | 4-Propanoyl-6-phenoxyphenol | | | |
| (132) | 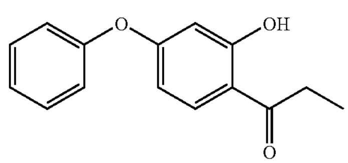 | 2-Propanoyl-5-phenoxyphenol | Procedure V, VI A/VI B. | — | 1. $^1$H-NMR 2. M.S. |
| (133) | 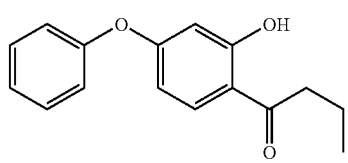 | 2-Butanoyl-5-phenoxyphenol | Procedrue V, VI A/VI B | 72–73 | 1. $^1$H-NMR 2. M.S. |
| (134) | 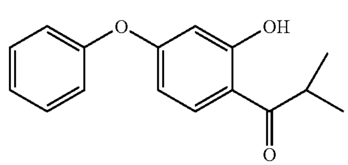 | 2-(2-methyl-propan-oyl)5-phenoxyphenol | Procedure V, VI A/VI B. | 63–65 | 1. $^1$H-NMR 2. M.S. |
| (135) | 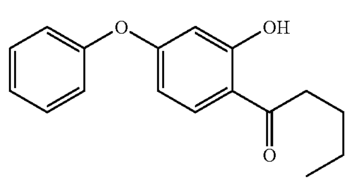 | 2-Pentanoyl-5-phenoxyphenol | Procedure V, VI A/VI B. | — | 1. $^1$H-NMR 2. M.S. |

TABLE 2-continued

| Comp. of form. | Structure | Name/CAS | Synthetic procedure-employed | MP [° C.] | Technique used for structure assignment |
| --- | --- | --- | --- | --- | --- |
| (136) | 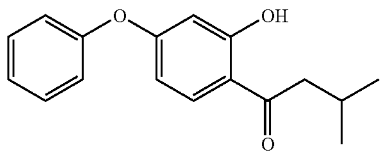 | 2-(3-Methyl butanoyl)-5-phenoxyphenol | Procedure V, VI A/VI B. | 53–54 | 1. $^1$H-NMR 2. M.S. |
| (137) | 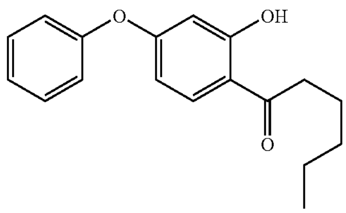 | 2-Hexanoyl-5-phenoxyphenol | Procedure V, VI A /VI B. | — | 1. $^1$H-NMR 2. M.S. |
| (138) | 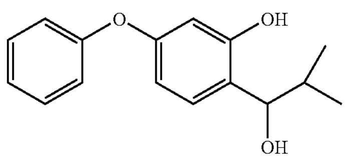 | 2-(1-Hydroxy-2-methylpropyl)-5-phenoxyphenol | NaBH$_4$ reduction of '16' | — | 1. $^1$H-NMR 2. M.S. |
| (104) | 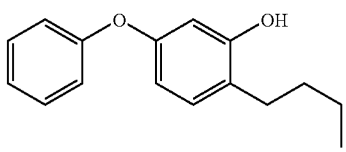 | 2-Butyl-5-phenoxy-phenol | Procedure V, VI A /VI B & III/VII. | — | 1. $^1$H-NMR 2. M.S. |
| (103) | 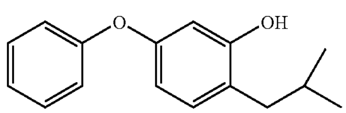 | 2-(2-Methylpropyl)-5-phenoxyphenol | Procedure V, VI A/VI B & III/VII. | — | 1. $^1$H-NMR 2. M.S. |
| (106) | 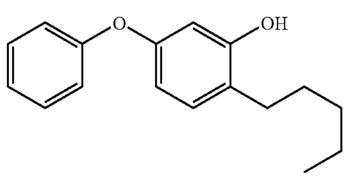 | 2-Pentyl-5-phenoxy-phenol | Procedure V, VI A /VI B & III /VII | — | 1. $^1$H-NMR 2. M.S. |
| (139) | 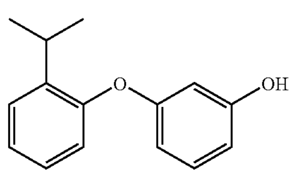 | 3-(2-Isopropyl)-phenoxyphenol | Procedure I & IV | — | 1. $^1$H-NMR 2. M.S. |
| (116) | 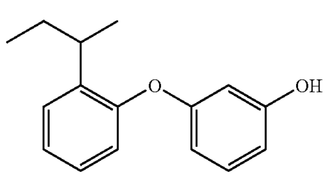 | 3-(2-sec-Butyl) phenoxyphenol | Procedure I & IV | — | 1. $^1$H-NMR 2. M.S. |
| (126) | 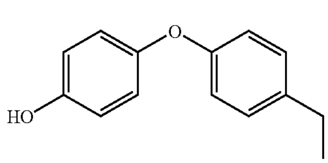 | 4-(4-Ethyl phenoxy)-phenol | Procedure I & IV | — | 1. $^1$H-NMR 2. M.S. |

TABLE 2-continued

| Comp. of form. | Structure | Name/CAS | Synthetic procedure-employed | MP [° C.] | Technique used for structure assignment |
|---|---|---|---|---|---|
| (140) | 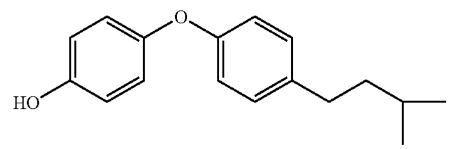 | 4-(4-(3-Methyl butyl) phenoxy) phenol 35065-13-5 | Procedure I & IV | — | 1. $^1$H-NMR 2. M.S. |
| (125) | 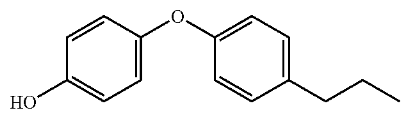 | 4-(4-Propyl phenoxy)-phenol | Procedure I, II, IV & III/VII | — | 1. $^1$H-NMR 2. M.S. |
| (141) | 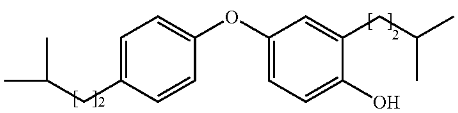 | 4-((3-Methyl butyl)-phenoxy)3-(3-methyl butyl)phenol | Procedure I, II, IV & III/VII | — | 1. $^1$H-NMR 2. M.S. |
| (142) | 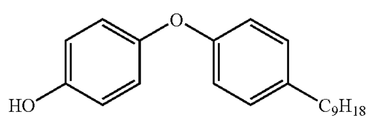 | 4-(4-Nonyl phenoxy)-phenol | Procedure I, II, IV & III/VII | 50–51 | 1. $^1$H-NMR 2. M.S. |
| (143) | 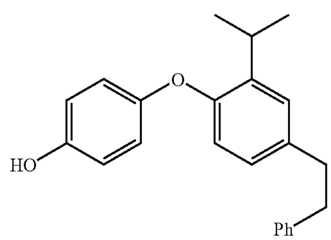 | 4-(2-Methylethyl-4-(2-phenylethyl)phenoxy)-phenol | Procedure I, II, IV & III/VII | — | 1. $^1$H-NMR 2. M.S. |
| (144) | 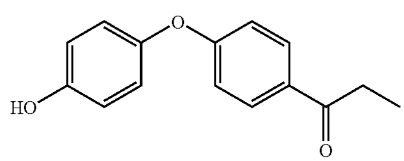 | 4-(4-Propionyl phenoxy)phenol | Procedure I, II & IV | — | 1. $^1$H-NMR 2. M.S. |
| (145) | 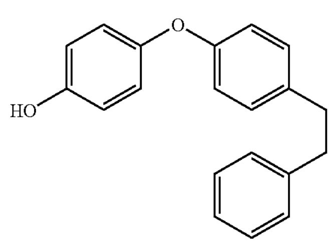 | 4-(4-(2-Phenyl ethyl)-phenoxy)phenol | Procedure I, II, IV & III/VII | 84–86 | 1. $^1$H-NMR 2. M.S. |
| (146) | 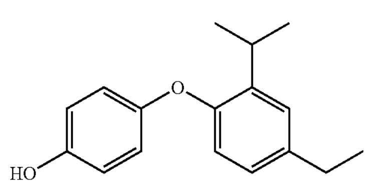 | 4-(4-ethyl-2-methylethyl-)phenoxy)-phenol | Procedure I, II, IV & III/VII | — | 1. $^1$H-NMR 2. M.S. |

TABLE 2-continued

| Comp. of form. | Structure | Name/CAS | Synthetic procedure-employed | MP [° C.] | Technique used for structure assignment |
|---|---|---|---|---|---|
| (147) | 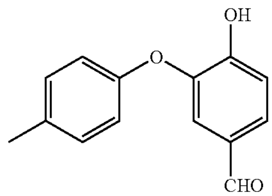 | 4-Hydroxyl-5-(4-methylphenoxy)benzaldehyde 136805-20-4 | Procedure I & IV | 88–90 | 1. $^1$H-NMR 2. M.S. |
| (148) | 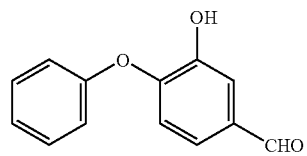 | 3-Hydroxyl-4-phenoxy benzaldehyde 35065-13-5 | Procedure I & IV | — | 1. $^1$H-NMR 2. M.S. |
| (149) | 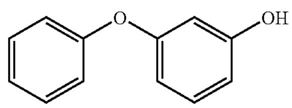 | 3-phenoxyphenol 713-68-8 | Procedure V | — | 1. $^1$H-NMR 2. M.S. |
| (150) | 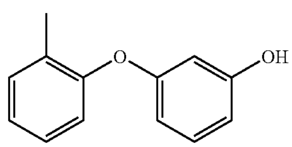 | 3-(2-methyl phenoxy)phenol | Procedure I & IV | — | 1. $^1$H-NMR 2. M.S. |
| (151) | 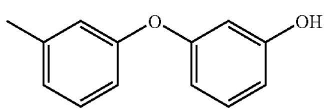 | 3-(3-methyl phenoxy)phenol | Procedure I & IV | — | 1. $^1$H-NMR 2. M.S. |
| (105) | 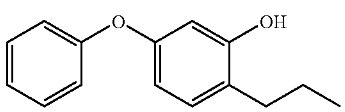 | 2-Propyl-5-phenoxyphenol | Procedure V, VI A/VI B & III/VII | — | 1. $^1$H-NMR 2. M.S. |
| (152) | 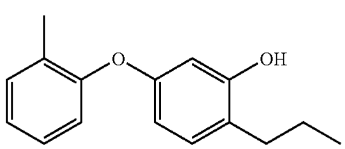 | 2-Propyl-5-(2-methylphenoxy)phenol | Procedure I, IV, VI A/VI B & III/VI | — | 1. $^1$H-NMR 2. M.S. |
| (153) | 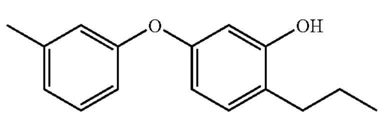 | 2-Propyl-5-(3-methylphenoxy)phenol | Procedure I, IV, VI A/VI B & III/VI | — | 1. $^1$H-NMR 2. M.S. |
| (154) | 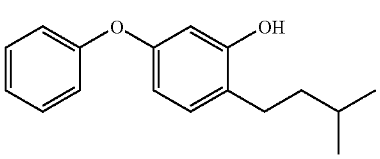 | 5-phenoxy-2-(3-methylbutyl)phenol | Procedure V, VI A/VI B & III/VI | — | 1. $^1$H-NMR 2. M.S. |
| (155) | 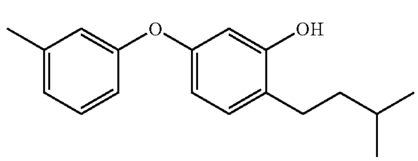 | 2-(3-methylbutyl)-5-(3-methylphenoxy)phenol | Procedure I, II, IV & III/VII | — | 1. $^1$H-NMR 2. M.S. |

TABLE 2-continued

| Comp. of form. | Structure | Name/CAS | Synthetic procedure-employed | MP [° C.] | Technique used for structure assignment |
|---|---|---|---|---|---|
| (156) | 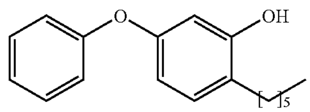 | 2-Hexyl-5-phenoxy phenol | Procedure V, VI A/VI B & III/VII | — | 1. $^1$H-NMR<br>2. M.S. |
| (157) | 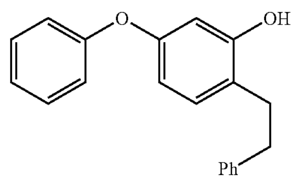 | 2-(2-phenylethyl)-5-phenoxy phenol | Procedure V, VI A/VI B & III/VII | 73–75° C. | 1. $^1$H-NMR<br>2. M.S. |
| (158) | 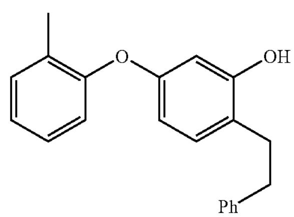 | 2-(2-phenylethyl)-5-(2-methyl phenoxy) phenol | Procedure I, IV, VI A/VI B & III/VII | — | 1. $^1$H-NMR<br>2. M.S. |
| (159) | 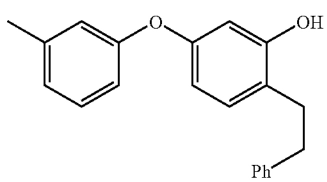 | 2-(2-phenylethyl)-5-(3-methyl phenoxy) phenol | Procedure I, IV, VI A/VI B & III/VII | — | 1. $^1$H-NMR<br>2. M.S. |
| (160) | 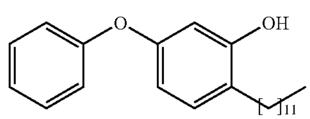 | 2-Dodecanoyl-5-phenoxy phenol | Procedure V, VI A/VI B & III/VII | — | 1. $^1$H-NMR<br>2. M.S. |
| (161) | 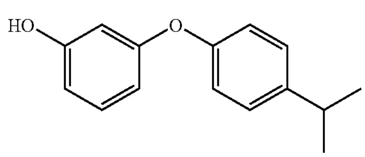 | 3-[4-(2-methyl ethyl)]phenoxy phenol | Procedure I & IV | — | 1. $^1$H-NMR<br>2. M.S. |
| (162) | 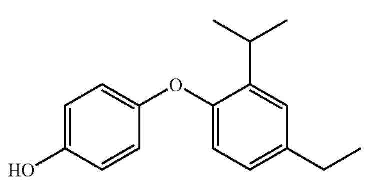 | 4-(2-methylethyl-4-ethyl)phenoxy phenol | Procedure I, II, IV & III/VII | — | 1. $^1$H-NMR<br>2. M.S. |
| (127) | 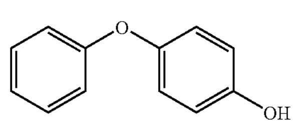 | 4-phenoxy phenol<br>831-82-3 | Procedure I & IV | 76–77 | 1. $^1$H-NMR<br>2. M.S. |
| (163) | 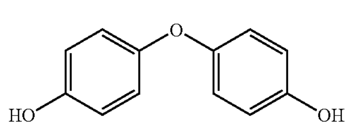 | 4-(4-hydroxy) phenoxy phenol<br>1965-09-9 | Procedure I & IV | — | 1. $^1$H-NMR<br>2. M.S. |

TABLE 2-continued

| Comp. of form. | Structure | Name/CAS | Synthetic procedure-employed | MP [° C.] | Technique used for structure assignment |
|---|---|---|---|---|---|
| (164) | 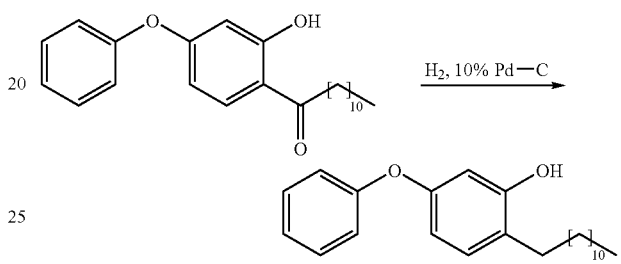 | 3-(4-hydroxy) phenoxy phenol 68100-19-6 | Procedure I & IV | 116–118 | 1. ¹H-NMR 2. M.S. |

General Synthesis of Hydroxydiphenylethers

General Procedure-I.

Example:

Ullmann condensations are carried out as per the procedure outlined by R. G. R. Bacon and O. J. Stewart, J. Chem. Soc., 1965 4953.

To a stirred solution of o-cresol 21.6 g. (0.2 mol) in 110 ml N, N-dimethyl acetamide under nitrogen atmosphere, was added o-bromoanisole 74.8 g (0.4 mole) followed by Cuprous oxide 28.62 g (0.4 mole). Reaction mixture refluxed for 24 hr at 165–167° C. It was cooled to room temperature and poured to 1 l water containing 100 ml concentrated HCl. Reaction mixture extracted with 3×150 mL ether. Organic extract washed with 10% NaOH solution to remove unreacted cresol. Solvent and excess of o-bromoanisole distilled off under reduced pressure. Product purified by chromatography over silica gel column.

yield=28 g.

% yield by theory=65%

General catalysts for Ullmann condensation: Cu, Cu2Cl2, bas. CuCO3, CuCl2, CuO, Cu2O, reaction in high boiling solvents as Pyridin, DMF, DMA, DMSO, Toluene, Xylene and others, bases are hydroxides/carbonates from group ½ metals General Procedure-II Example:

Acylation of methoxy diphenyl ether.

Isovelaroyl chloride 1.2 g (0.01 mole) and ethylene dichloride (10 ml) were mixed and cooled to 0° C. with stirring. Anhydrous AlCl₃ 2.7 g (0.02 mole) added portionwise maintaining temp. below 5° C. p-Methoxy diphenyl ether 2 g (0.01 m) added dropwise during 15 minutes. Stirring continued for 1 hr at 0–5° C. Reaction mixture added to 100 ml of cold water with vigorous stirring, followed by extraction with 50 ml ethylene dichloride. Organic layer separated, washed with 50 ml water and dried briefly over anhy. Na₂SO₄ Solvent distilled under reduced pressure to get the crude product. It was purified over silica gel column using hexane:ethyl acetate as eluent.

Yield: 2.46 g.

% yield by theory: 85–90%

General Friedl-Crafts acylation catalysts: Lewis acids as AlCl₃, ZnCl₃, FeCl₃, BCl₃, BF₃, transition metal trifluorosulfonates (eg. Sc(OTf)₃) reaction in inert solvents as EDC, CH2Cl2, CS2, Nitrobenzene General Pocedure-III Example:

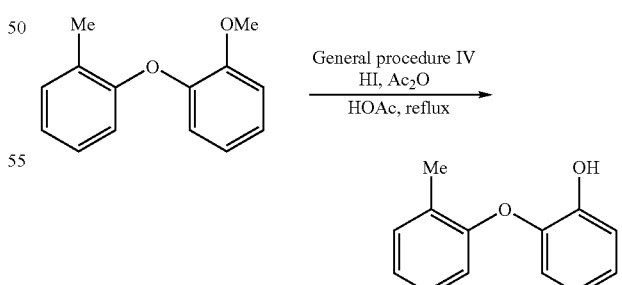

Hydrogenation of Keto to methylene.

To a 125 ml autoclave, a solution of Keto compound 3.67 g (0.01 mole) in 50 ml ethanol was charged, followed by 10 ml gl. acetic acid,10% Pd-C (5 mg), 0.1 ml perchloric acid and flushed twice with hydrogen. Reaction mixture hydrogenated at an autoclave temp. of 65° C. and pressure of 100–110 psi for 4–6 hr. Completion of the reaction was followed by TLC. Reaction mixture cooled to room temperature, pressure released and filtered. Filtrate was added to 200 ml water. Ethylene dichloride (100 ml) was added, organic layer washed with 2×50 ml 5% NaHCO₃ solution and dried over anhy. Na₂SO₄. Solvent distilled off under reduced pressure to get the product.

Yield: 3.33 g.

% yield by theory: 90–95%

General Procedure-IV

Example:

Demethylation of methoxy ether to phenol.

Methyl ether 14 g (0.065 mole), acetic acid 25 ml , hydroiodic acid 25 ml, acetic anhydride 20 ml. were mixed and refluxed under stirring at 105–110° C. for 1 hr. Reaction mixture poured into 1 L ice cold water, decolorized with Sodium sulphite solution, neutralized with saturated NaHCO$_3$ Solution (2×100 ml) and extracted with DCM (3×100 ml). Organic layer washed with water, dried over Na$_2$SO$_4$. Crude reaction mixture chromatographed over silica column to get the pure product.

Yield: 10 g

% yield by theory: 75%

General demethylating agents as AlCl$_3$, BCl$_3$, BF$_3$, HBr, pyridinium×HCl

General Procedure-V

Example:

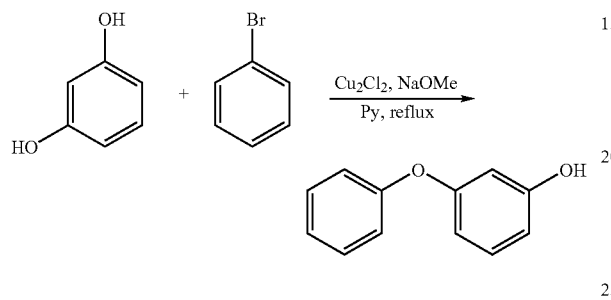

Preparation of m-phenoxyphenol

To a stirred solution of 49.5 g (0.45 mol) of resorcinol in 75 ml dry pyridine under nitrogen atmosphere, 16.2 g (0.3 mol) of Sodium methoxide was added. Heating started and methanol fractionally distilled off over a period of 0.5 hr. Bromobenzene, 142 g (0.9 mole) was run in to the reaction mixture followed by 2.2 g, of Cuprous chloride. Reaction mixture heated under reflux for 3–4 hr, pyridine distilled off while the pot temperature rose to 150° C. The residue was poured into 50 ml conc. HCl in 120 ml water and stirred. Organic material extracted in 200 ml benzene followed by washing with 25 ml of 20% HCl. Organic layer extracted with 100 ml of 10% NaOH solution followed by a second extraction With 20 ml of 10% NaOH. The combined aqueous extracts were acidified with, HCl$_{conc}$, liberated m-phenoxy phenol was extracted into benzene (300 ml). From the organic layer benzene was removed by distillation. Crude product purified by filtration over a column of silica.

Yield: 35 g

% yield by theory: 40–42%

Catalysts for Ullmann condensation see Proc. I

General Procedure-VI-A

Example:

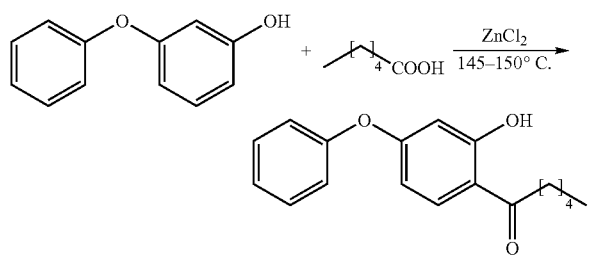

Acylation of m-phenoxy phenol

Hexanoic acid 12.87 g (0.11 mole) added to fused ZnCl$_2$ 6.50 g(0.15 mol), dissolved at 145–150° C. To the above reaction mixture m-phenoxy phenol 5.9 g(0.032 mole) was added. Reaction mass stirred at 145–150° C. for 3 hr. It was cooled to room temperature and poured over 250 ml cold water, washed with sat. NaHCO$_3$ solution (2×150 ml), extracted with ethyl acetate (2×100 ml). Organic extract dried over Na$_2$SO$_4$. Solvent distilled off under reduced Pressure. Crude product purified by chromatography over silica gel.

Yield: 2.5 g.

% yield by theory: 25–30%

General Procedure-VI-B

Example:

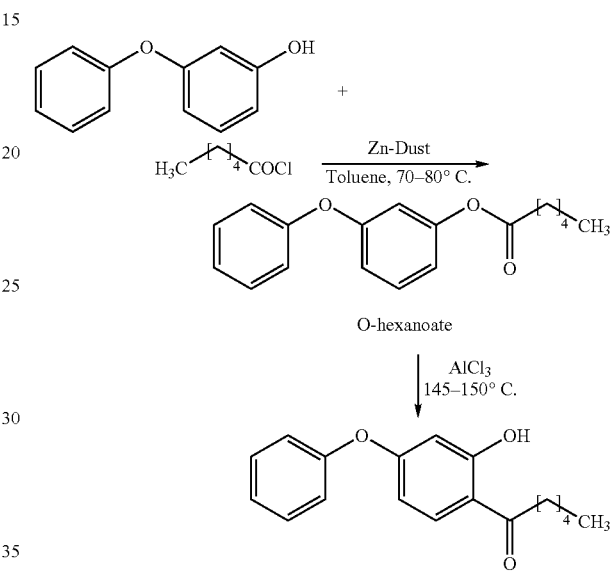

O-acylation of m-phenoxyphenol

Hexanoyl chloride 7.70 g (57.24 mmol) in 250 ml dry toluene was stirred with activated Zn dust 3.74 g (57.24 mmol) at room temperature for 15 minutes, m-phenoxy phenol 4.5 g (24.2 M mole) in 150 ml toluene added and the reaction mixture stirred at 70 to 75° C. for 30 minutes. Reaction mixture cooled to room temperature & filtered. Organic layer washed with 100 ml of 20% K$_2$CO$_3$ Solution followed by second washing with 15 ml of 20% K$_2$CO$_3$ Solution. Toluene layer washed with water, dried over Na$_2$SO$_4$. Solvent distilled off under reduced pressure to get the product.

Yield: 6 g.

% yield by theory: 85%

Acylation also with carboxylic acid anhydrides

Fries rearrangement

O-hexanoate 0.8 g (2.81 mmol) and AlCl$_3$ 0.45 g (3.47 mmol) were mixed together in a round bottom flask. After 4 hr at 145–150° C., reaction mixture cooled to room temperature and worked up by pouring over 50 ml 1:1 HCl (50 ml) followed by extraction in DCM (100 ml). Organic layer washed with water. Solvent evaporated off under reduced pressure. Crude reaction mass purified by silica gel column chromatography to get the pure product.

Yield : 0.6 g

% yield by theory: 75%

General Procedure-VII

Example:

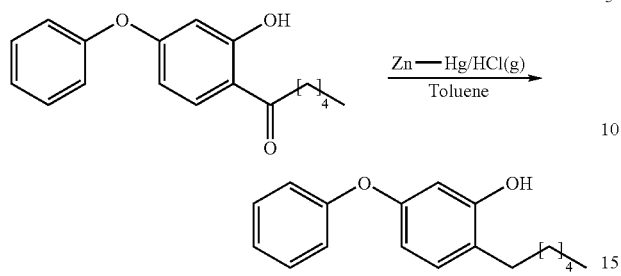

Reduction of keto to methylene by Clemmenson's method

Zinc amalgam was prepared from 12 g of Zn dust, 0.9 g of mercury (II) chloride in 20 ml water and 2–3 ml $HCl_{conc}$. This was added to the solution of keto compd 1.5 g (5.28 mmol) in 25 ml of toluene & 20 ml $HCl_{conc}$. HCl gas bubbled into reaction mixture for 2 hr. 50 ml of toluene was added and toluene layer separated and washed with water. Solvent distilled off under reduced pressure to get the product.

Yield: 1.45 g

% yield by theory=85–90%

Reduction also succeeds with $H_2$, see Proc. III

EXAMPLE 5

Preparation of the Compound of Formula

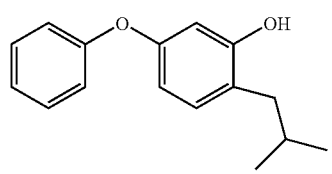

(103)

Reaction scheme:

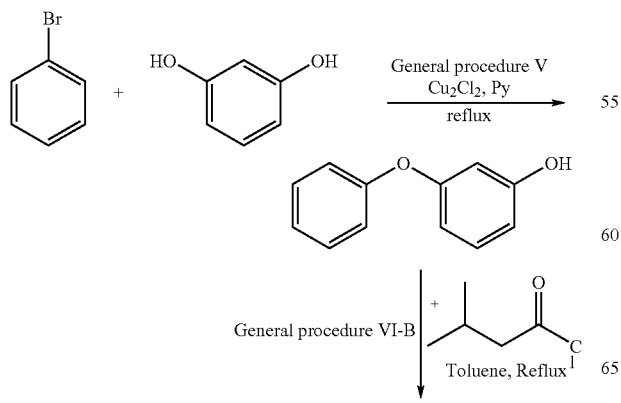

EXAMPLE 6

Preparation of Compound of Formula

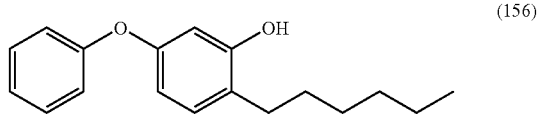

(156)

Reaction scheme:

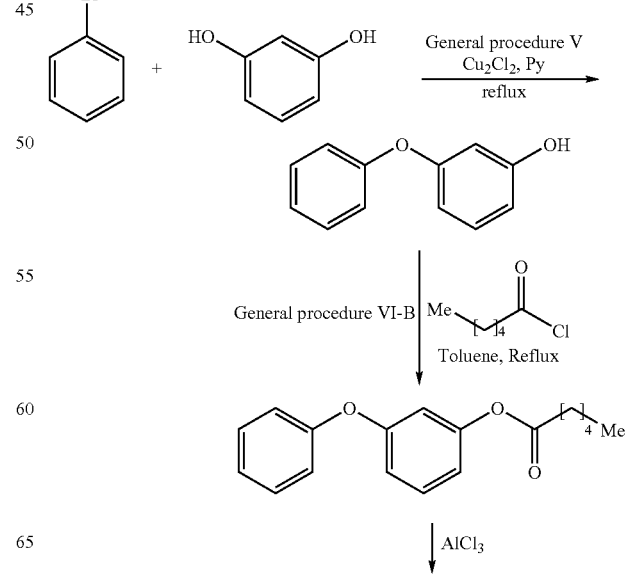

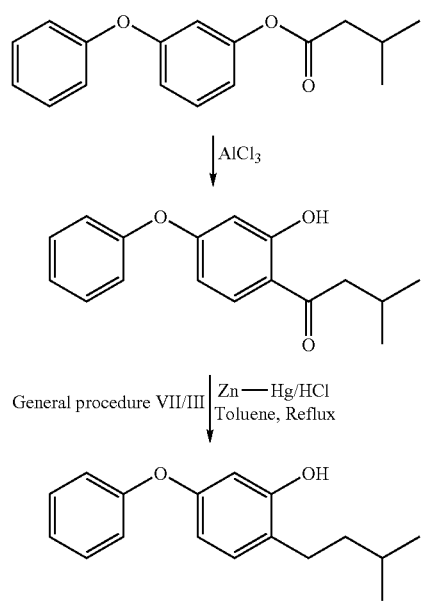

EXAMPLE 7

Preparation of Compound of Formula (105)

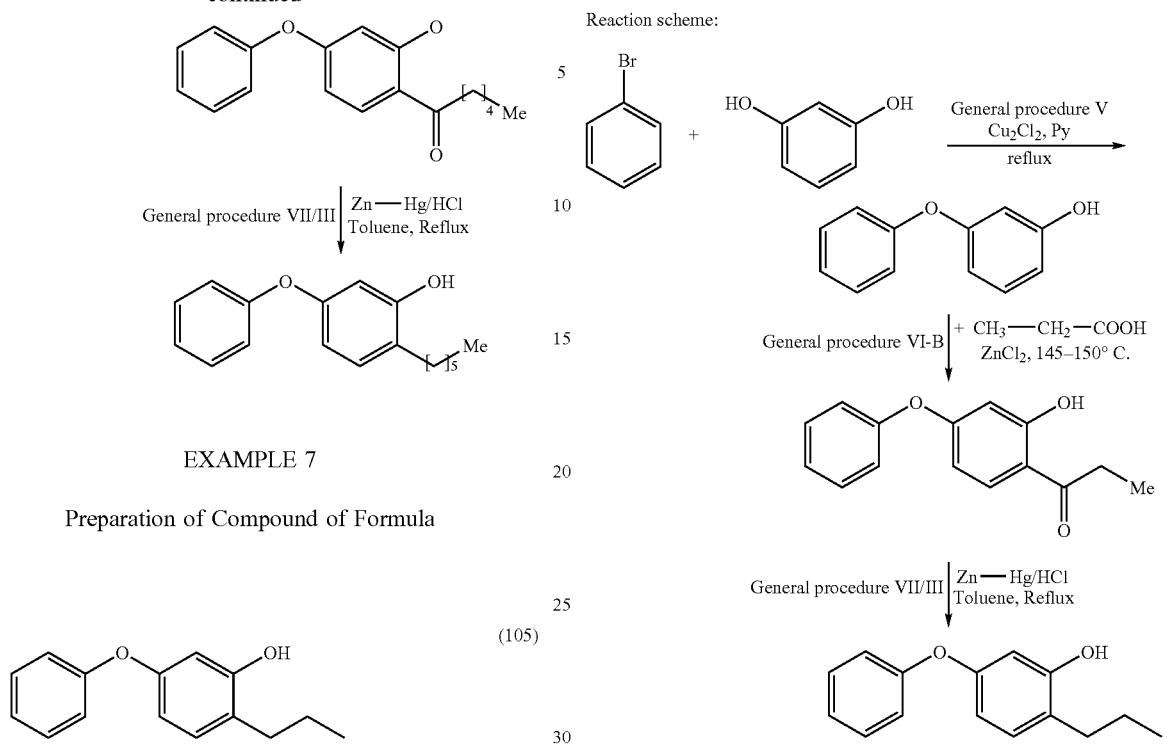

Reaction scheme:

TABLE 3

| Compound | Reaction Protocols | m/e (M + 1) | 1H NMR (d ppm) |
|---|---|---|---|
| (105) | General procedure V, VIA/VIB & III/VII | 229 | 0.9–1.0(t, 3H, Me), 1.55–1.65(m, 2H, —$CH_2$—), 2.4–2.5(t, 2H, —$CH_2$—), 4.8(s, 1H, —OH), 6.4–6.45(d, 1H, $H^6$Ar—H), 6.45–6.50(dd, 1H, $H^4$Ar—H), 6.95–7.05(m, 4H, $H^{2'}$, $H^{3'}$, $H^{5'}$, $H^{6'}$Ar—H), 7.25(d, 1H, $H^3$Ar—H), 7.25–7.3(m, 1H, $H^4$Ar—H) |
| (154) | General procedure V, VIA/VIB & III/VII | 257 | 0.9–1.0(d, 6H, iso-pr), 1.4–1.55(m, 2H, >$CH_2$, >CH—), 2.6(t, 2H, —$CH_2$—), 4.8(s, 1H, —OH), 6.4(d, 1H, $H^6$Ar—H), 6.55–6.60(dd, 1H, $H^4$Ar—H), 6.9–7.05(m, 4H, $H^{2'}$, $H^{3'}$, $H^{5'}$, $H^{6'}$Ar—H), 7.25(d, 1H, $H^3$Ar—H), 7.25–7.3(m, 1H, $H^4$Ar—H) |
| (156) | General procedure V, VIA/VIB & III/VII | 271 | 0.9–1.0(t, 3H, Me), 1.2–1.4(m, 6H, —$CH_2$—), 1.45–1.65(m, 2H, —$CH_2$—), 2.45–2.6(t, 2H, —$CH_2$—), 5.0(s, 1H, —OH), 6.4–6.5(d, 1H, $H^6$Ar—H), 6.50–6.60(dd, 1H, $H^4$Ar—H), 6.9–7.2(m, 4H, $H^{2'}$, $H^{3'}$, $H^{5'}$, $H^{6'}$Ar—H), 7.3(d, 1H, $H^3$Ar—H), 7.4(m, 1H, $H^4$Ar—H) |

EXAMPLE 8

Synthesis of 4-(2.5-Dialkylphenoxy)-Phenols

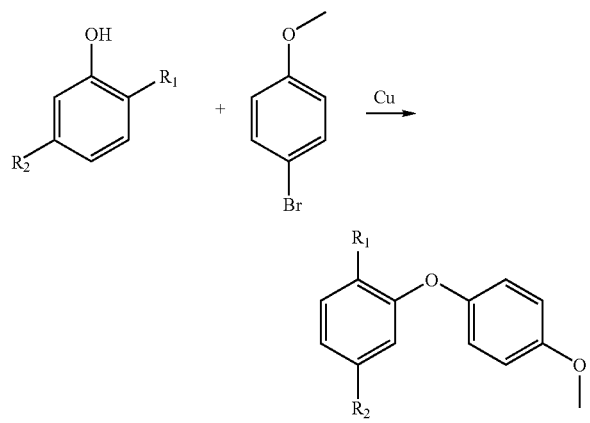

The mixture of 0.05 mol 2.5-Dialkylphenol, 2.8 g (0.05 mol) KOH, 0.4 g (0.006 mol) copper powder and 50 g (0.25 mol) bromo anisole is heated in a standard reaction apparatus, equipped with a water trap, to 160° C. for 5 h. After cooling the reaction mass is suspended in toluene and filtrated. After distilling off the solvent and excess reagent the product is isolated by distillation at 125° C./0.01 mbar

| $R_1$ | $R_2$ | Yield |
|---|---|---|
| Me | Me | 4.6 g (40%) |
| Me | i-Propyl | 6.4 g (50%) |

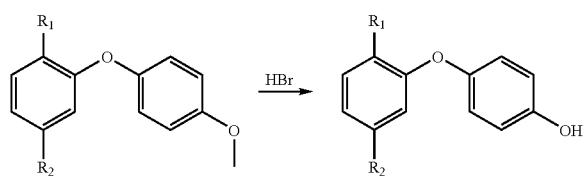

0.02 mol of the 4-(2,5-Dialkylphenoxy)-methoxybenzene and 30 ml HBr (47% solution in water) are heated to reflux in 100 ml acetic acid for 4 h. After cooling and distilling off acetic acid the reaction mass is dissolved in 100 ml methylene chloride and washed with 200 ml water with pH adjusted to pH 10 with 10% NaOH. Produkt is isolated from the organic phase by distillation at 160° C./0.01 mbar, colourless oils.

| $R_1$ | $R_2$ | Yield |
|---|---|---|
| Me | Me | 2.2 g (52%) |
| Me | i-Propyl | 2.4 g (60%) |

Data $R_1=R_2=$Me:

Elementary Analysis:

|  | C | H | O |
|---|---|---|---|
| calc. | 78.48 | 6.59 | 14.93 |
| found | 77.84 | 6.58 | 15.19 |

1 H-NMR (CDCl$_3$): 2.15 (3H,s,CH$_3$), 2.20 (3H,s,CH$_3$), 4.65 (1H,s,OH), 6.55–7.05 (7H,m,arom. H)

Mass spectrum: m/z [M+·]=214

Data $R_1$=Me, $R_2$=i-Propyl:

Elementary Analysis:

|  | C | H | O |
|---|---|---|---|
| calc. | 79.30 | 7.49 | 13.21 |
| found | 77.82 | 7.30 | 13.61 |

1H-NMR (CDCl$_3$): 1.05 (3H,s,CH$_3$), 1.08 (3H,s,CH$_3$), 2.10 (3H,s,CH$_3$), 2.70 (1H,sCH), 4.85 (1H,s,OH), 6.60–7.05 (7H,m,arom. H)

Mass spectrum: m/z [M+·]=242

EXAMPLE 9

Synthesis of 4-(2-t-Butyl-5-methylphenoxy)phenol

Reaction Scheme:

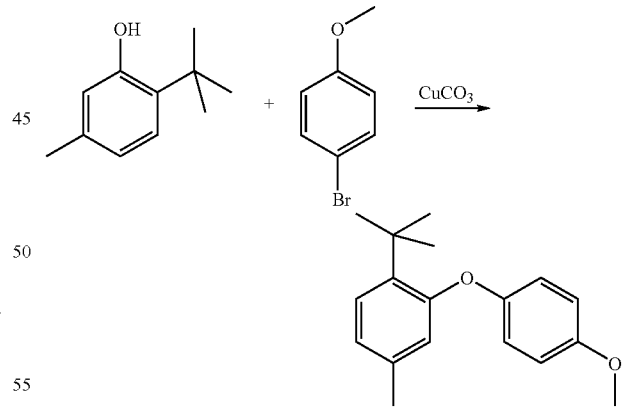

The mixture of 16.4 g (0.1 mol) 2-t-butyl-5-methylphenol and 1.8 g (0.03 mol) KOH in 100 ml xylene is heated in a standard reaction apparatus, equipped with a water trap, to reflux until no more water is distilling. After addition of 0.2 g basic copper carbonate and 18.7 g (0.1 mol) bromo anisole the mixture is heated to reflux for 20 h. After cooling the reaction mass is filtrated and solvent and excess reagents are distilled off. The product is isolated by distillation at 100° C./0.01 mbar.

Yield: 7.1 g (81%).

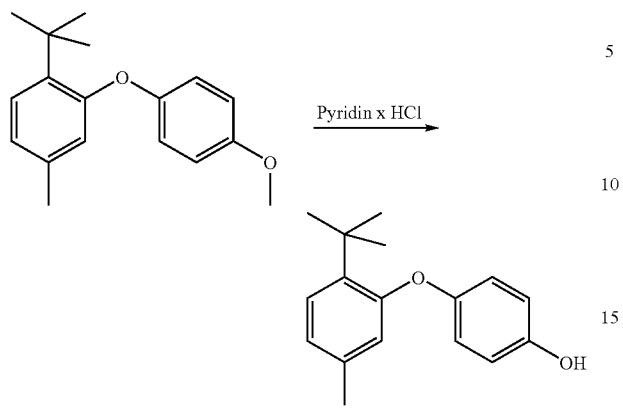

7.1 g (0.026 mol) of 4-(2-t-Butyl-5-methylphenoxy)-methoxybenzene are heated with 15.0 g (0.13 mol) pyridinium hydrochloride to 180° C. for 6 h. After cooling water is added and the reaction mass is extracted with xylene. The product is distilled after evaporation of xylene at 130° C./0.01 Torr and recrystallized from petrol ether (80–110 to yield colourless crystals (mp 102° C.).

Yield: 4.6 g (69%)

Elementary Analysis:

|  | C | H | O |
|---|---|---|---|
| calc. | 79.65 | 7.86 | 12.48 |
| found | 78.96 | 7.55 | 11.59 |

1H-NMR (CDCl$_3$): 1.41 (9H,s,C(CH$_3$)$_3$), 2.21 (3H,s, CH$_3$), 4.75 (1H,s,OH) (7H,m,arom.H)

Mass spectrum: m/z [M+·]=256

Microbiological data of the above compounds (MIC in ppm):

TABLE 4

| | Substance | | |
|---|---|---|---|
| Microorganisms | $R_1$ = t-Butyl $R_2$ = Me | $R_1$ = Me $R_2$ = i-Propyl | $R_1$ = $R_2$ = Me |
| *Staphylococcus aureus* ATCC 6538 | 6.75 ppm | 6.25 ppm | 50.0 ppm |
| *Staphylococcus epidermidis* ATCC 12228 | 3.4 ppm | 6.25 ppm | 25.0 ppm |
| *Corynebacterium xerosis* ATCC 373/ATCC 7711 | 3.4 ppm | 3.125 ppm | 25.0 ppm |
| *Staphylococcus hominis* DSM 20328 | | 6.25 ppm | — |
| *Corynebacterium minutissimum* ATCC 23348 | 3.4 ppm | 6.25 ppm | 25.0 ppm |
| *Propionibacterium acnes* ATCC 11829 | 5 ppm | 10 ppm | — |
| *Escherichia coli* NCTC 8196 | >100 ppm | >200 ppm | >200 ppm |
| *Proteus vulgaris* ATCC 6896 | >100 ppm | >200 ppm | >200 ppm |
| *Pseudomonas aeruginosa* CIP A-22 | >100 ppm | >200 ppm | >200 ppm |
| *Candida albicans* ATCC 10231 | 12.5 ppm | 12.5 ppm | 25.0 ppm |
| *Aspergillus niger* ATCC 6275 | 6.75 ppm | 50 ppm | — |
| *Epidermophyton floccosum* CBS 55384 | 1.65 ppm | <3.125 ppm | — |
| *Trichophyton mentagrophytes* ATCC 9553 | 3.4 ppm | 6.25 ppm | — |
| *Trichophyton rubrum* DSM 4167 | 10 ppm | 5 ppm | — |
| *Malassezia furfur* DSM 6171 | 2.5 ppm | — | — |
| *Actinomyces viscosum* DSM 43329 | 5 ppm | 80 ppm | — |
| *Porphyromonas gingivalis* DSM 20709 | 1.25 ppm | 5 ppm | — |
| *Selenomonas artemidis* ATCC 43528 | 5 ppm | 10 ppm | — |
| *Streptococcus sobrinus* DSM 20742 | 5 ppm | 5 ppm | — |

What is claimed is:

1. An antimicrobial method, which comprises contacting a substrate with an antimicrobially effective amount of a hydroxydiphenyl ether compound of the formula

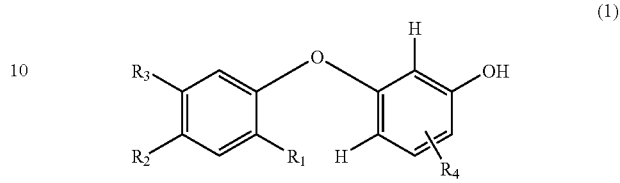

(1)

wherein, $R_2$ is hydrogen, $C_1$–$C_{20}$alkyl, hydroxy substituted $C_1$–$C_{20}$alkyl or $C_1$–$C_6$alkylcarbonyl;

$R_1$ and $R_3$ are independently of each other hydrogen or $C_1$–$C_{20}$alkyl; and $R_4$ is hydrogen, $C_3$–$C_5$alkyl, hydroxy substituted $C_1$–$C_{20}$alkyl, $C_1$–$C_6$alkylcarbonyl or $C_5$–$C_7$cycloalkyl, with the proviso that when $R_4$ is hydrogen, $R_1$ is $C_3$–$C_4$ alkyl and $R_3$ is hydrogen.

2. An antimicrobial method according to claim 1, wherein a compound of formula

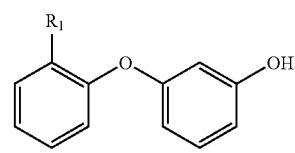

(6)

wherein $R_1$ is $C_3$–$C_4$alkyl is employed.

3. An antimicrobial method according to claim 1, wherein a compound of formula

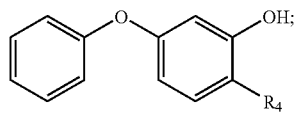 (7)

wherein R$_4$ is C$_3$–C$_5$alkyl is employed.

4. An antimicrobial method according to claim 1 which is carried out during finishing of undyed and dyed or printed fibre materials.

5. A method according to claim 1 for the antimicrobial treatment of skin, mucous membranes or hair which comprises applying an antimicrobially effective amount of a compound of the formula (1) as defined in claim 1 thereto.

6. A method of use of a compound of formula (1) as defined in claim 1 which comprises the incorporation of an antimicrobially effective amount of said compound into polymeric materials or the antimicrobial finishing of said polymeric materials with an antimicrobially effective amount of said compound as defined in claim 1.

7. A method according to claim 1 for the antimicrobial treatment of a hard surface which comprises applying to the hard surface an antimicrobially effective amount of a compound of the formula (1) as defined in claim 1.

8. A method for the antimicrobial treatment of teeth and gums which comprises applying an antimicrobially effective amount of a compound of the formula (1) as defined in claim 1 thereto.

9. An antimicrobial method according to claim 1, wherein a personal care composition comprising at least one compound of formula (1) as defined in claim 1 and a cosmetically tolerable carrier or auxiliary is employed.

10. An antimicrobial method according to claim 1, wherein an oral care composition comprising at least one compound of formula (1) as defined in claim 1 and a carrier or auxiliary is employed.

11. An antimicrobial method according to claim 1, wherein a detergent composition comprising at least one compound of formula (1) as defined in claim 1 and a carrier or auxiliary is employed.

* * * * *